US012661102B2

(12) United States Patent　　　　(10) Patent No.:　US 12,661,102 B2
Gelber et al.　　　　　　　　　　　　(45) Date of Patent:　Jun. 23, 2026

(54) TLIF DISTRACTION AND RETRACTION

(71) Applicant: GLOBUS MEDICAL, INC., Audubon, PA (US)

(72) Inventors: Jared Gelber, Philadelphia, PA (US); Damien Kahmer, Warrington, PA (US); Robert Ryan, Middletown, PA (US); Michael Webster, Paramus, NJ (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 19/038,961

(22) Filed: Jan. 28, 2025

(65) Prior Publication Data

US 2025/0169808 A1　　　May 29, 2025

Related U.S. Application Data

(63) Continuation of application No. 17/752,346, filed on May 24, 2022, now Pat. No. 12,207,811.

(51) Int. Cl.
| | |
|---|---|
| *A61B 17/02* | (2006.01) |
| *A61F 2/46* | (2006.01) |
| *A61B 17/70* | (2006.01) |
| *A61F 2/44* | (2006.01) |

(52) U.S. Cl.
CPC ........ A61B 17/025 (2013.01); A61B 17/0206 (2013.01); A61F 2/4611 (2013.01); A61B 2017/0256 (2013.01); A61B 17/7032 (2013.01); A61F 2/4455 (2013.01)

(58) Field of Classification Search
CPC .............. A61B 17/025; A61B 17/0206; A61B 17/7032; A61B 2017/0256; A61F 2/4455; A61F 2/4611
See application file for complete search history.

(56) References Cited

U.S. PATENT DOCUMENTS

| | | | | |
|---|---|---|---|---|
| 8,821,394 | B2 * | 9/2014 | Hawkins ............ | A61B 17/0293 |
| | | | | 600/214 |
| 9,271,711 | B2 * | 3/2016 | Hawkins ............ | A61B 17/0206 |
| 2008/0077139 | A1 * | 3/2008 | Landry .............. | A61B 17/7085 |
| | | | | 606/103 |
| 2010/0286486 | A1 * | 11/2010 | Parker ................ | A61B 17/1757 |
| | | | | 600/235 |
| 2012/0265021 | A1 * | 10/2012 | Nottmeier ................ | A61B 1/32 |
| | | | | 606/279 |
| 2018/0249992 | A1 * | 9/2018 | Truckey ............... | A61B 17/025 |
| 2019/0231334 | A1 * | 8/2019 | Serokosz ........... | A61B 17/7076 |

* cited by examiner

*Primary Examiner* — Jessica Weiss

(57)　　　　　　　ABSTRACT

Distractor and retractor systems and methods of using the same. A pedicle-based distractor assembly may include a base supporting a distraction rack, a pair of moveable arms coupled to the distraction rack, a connector at the end of each arm, each connector having a through-opening, and a pair of distractor elements each configured to attach to a pedicle screw. Each distractor element may be positioned through the through-opening in the respective connector. The distractor elements are modular such that different types of distractor elements, such as headless posts, pre-assembled posts, or minimally invasive towers, are interchangeable with the connectors. The assembly may also include a retractor assembly with a medial retractor blade for retracting soft tissue.

17 Claims, 22 Drawing Sheets

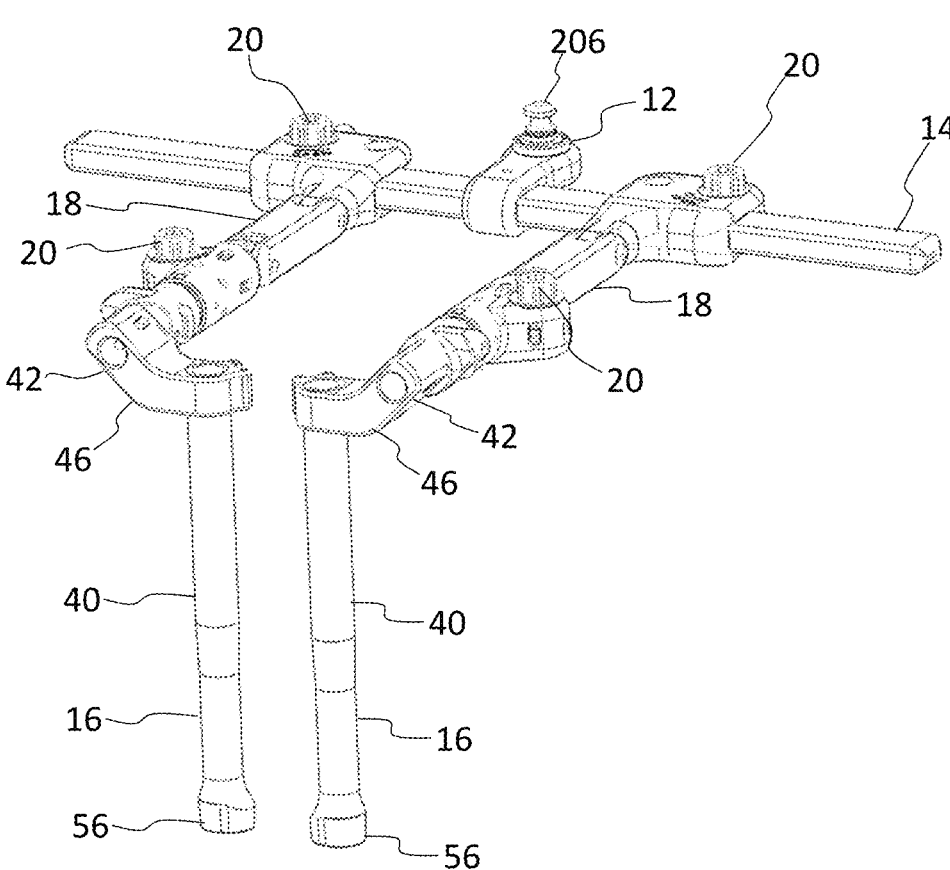
FIG. 1

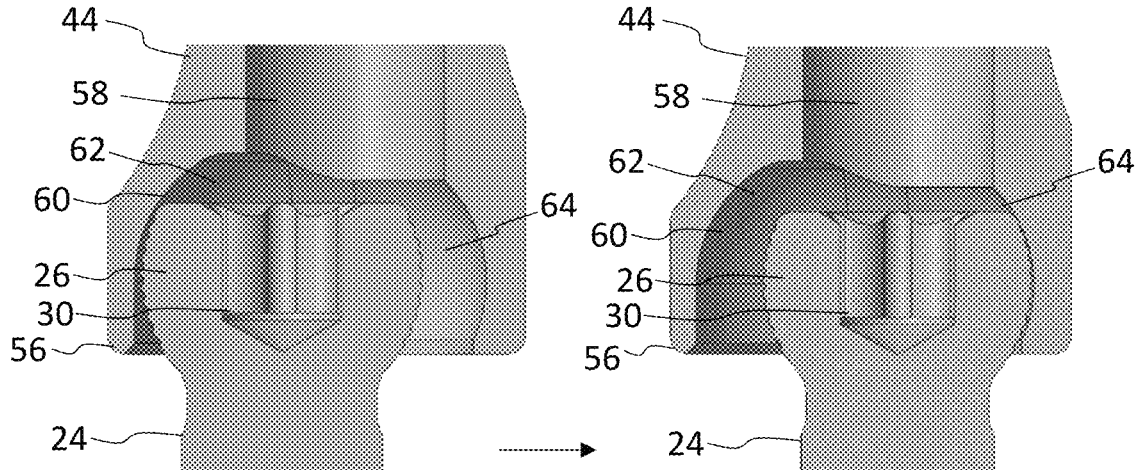
FIG. 3A                    FIG. 3B

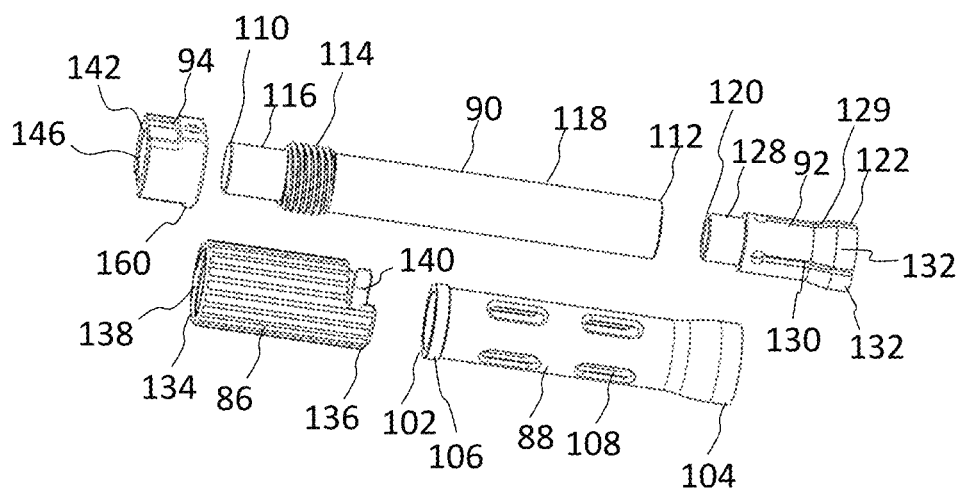
FIG. 5

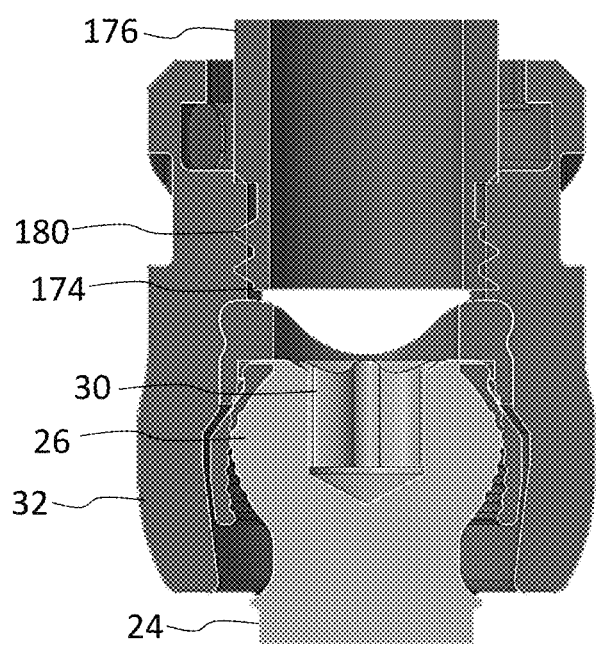
FIG. 10A
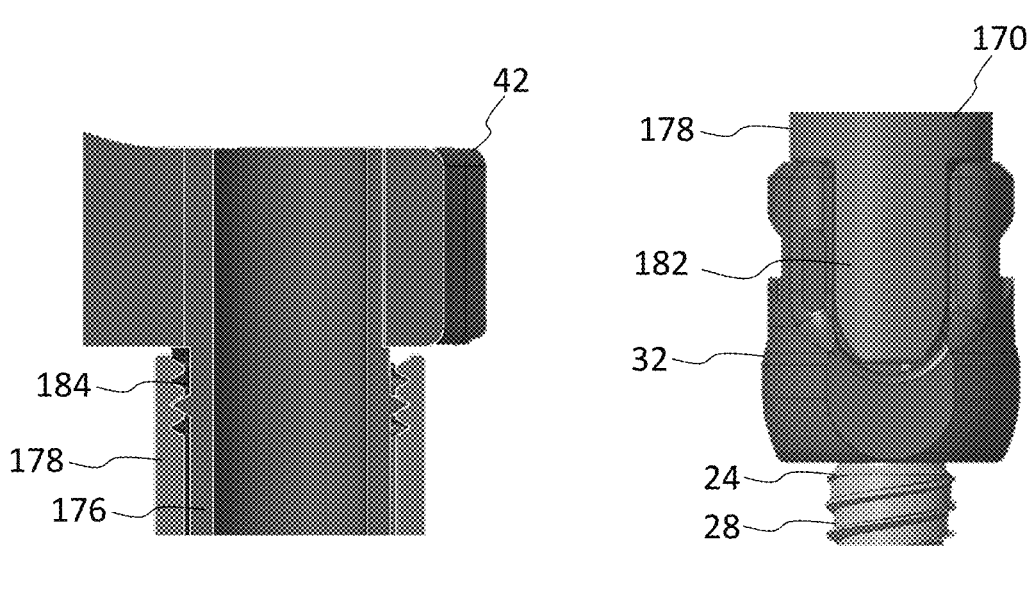
FIG. 10B                  FIG. 10C

FIG. 14A                    FIG. 14B

TLIF DISTRACTION AND RETRACTION

CROSS-REFERENCE TO RELATED APPLICATIONS

The present application is a continuation of U.S. patent application Ser. No. 17/752,346, filed on May 24, 2022, which is incorporated herein by reference.

FIELD OF THE INVENTION

The present disclosure generally relates to devices and systems for performing pedicle-based surgical distraction and/or retraction and methods of use thereof.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated through a surgical procedure that may include, for example, immobilizing a portion of the spine. These treatments may involve, for example, replacing a damaged disc with an intervertebral implant and/or securing the adjacent vertebrae, for example, with a combination of screws and rods. For correction of a collapsed disc causing impingement of one or more nerve roots, for example, the disc space may be restored back to or near its original height and the collapsed disc may be replaced with a device and/or bone graft material.

In order to perform these procedures, a surgical opening is created, and a device such as a retractor may be used to enlarge the opening and facilitate access to the surgical site. The retractor may typically include one or more blades that can be adjusted to establish, provide, and/or maintain an appropriate opening that minimizes trauma to surrounding tissue. A distractor may also be used to distract the disc space, for example, by placing a portion of the distractor between vertebral bodies or by using adjacent level pedicle screws.

By using a pedicle-based system, the assembly can perform the functions of both a distractor and a retractor. For example, the pedicle screws may be configured to simultaneously facilitate distraction of the disc space and a blade may provide for soft tissue retraction. There is a need, however, for improved distractors/retractors which provide pedicle-based distraction and/or soft tissue retraction.

SUMMARY OF THE INVENTION

To meet this and other needs, devices, systems, and methods for performing pedicle-based surgical distraction and/or retraction are provided. In particular, a modular pedicle-based distraction assembly may include interchangeable distractor elements, such as headless posts, pre-assembled posts, or minimally invasive towers. The pedicle-based distractors are configured to widen the collapsed disc space, thereby enlarging the disc space. The pedicle-based distraction also acts as a landmark method that pinpoints the surgical safe-zone. With pedicle-based distraction, tissue retraction may also be used to view and access the surgical site. For example, a retractor assembly may be attached to the distraction assembly. The retractor assembly may include a medial retractor blade configured to retract soft tissue.

According to one embodiment, a pedicle-based distractor assembly includes a base supporting a distraction rack, a pair of moveable arms coupled to the distraction rack, a connector at the end of each arm, each connector having a through-opening, and a pair of distractor elements each having a proximal end and a distal end. Each distractor element is positionable into the through-opening in the respective connector and the distal end of each distractor element is configured to attach to a pedicle screw. The distractor elements are modular such that different types of distractor elements are interchangeable with the connectors.

The pedicle-based distractor assembly may include one or more of the following attributes. Each distractor element may include a headless post, a pre-assembled post, or a minimally invasive tower. The through-opening may define a bow-tie shape with two opposed concave wings. The distractor element may include a headless post having a cap, and the through-opening receives the cap having a pair of opposed convex wings defined by opposite recesses, wherein the convex wings of the cap fit in the concave wings of the through-opening. A lower portion of the cap may include a flat face with a bore and an opposite side of the cap includes a shelf receivable in a corresponding notch in the connector. The cap may be retained in the through-opening with a set screw threaded into the bore in the cap. The distractor element may include a minimally invasive tower with a pair of tulip extenders receivable in the concave wings of the through-opening in the connector. The assembly may also include an optional retractor assembly with a medial retractor blade configured to retract soft tissue.

According to one embodiment, a pedicle-based distractor assembly includes a pair of headless posts extending from a proximal end to a distal end along a central longitudinal axis. Each headless post defines a channel through its length terminating at a screw head receiving chamber at the distal end with an open bottom for receiving a screw head of a pedicle screw. The screw head receiving chamber includes two screw-retaining sections. When the pedicle screw is aligned with the channel, an instrument is configured to be inserted through the channel to engage the pedicle screw.

The pedicle-based distractor assembly may include one or more of the following attributes. The two screw retaining-sections may include an open section and a contoured section. In the open section, the pedicle screw is free to translate into the contoured section. The open section may be spherical in shape with a volume greater than a volume of the contoured section. The open section may have a depth greater than the depth of the contoured section. The open section rests on the screw head and allows for free movement and positioning of the headless post. The contoured section may be spherical with a size and shape generally dimensioned to match an outer geometry of the screw head. The contoured section captures the screw head when a force is applied in a direction perpendicular to the pedicle screw and away from the open section. The distractor assembly may further include a base supporting a distraction rack, a pair of moveable arms coupled to the distraction rack, and a connector at the end of each arm configured for retaining the proximal ends of the headless posts.

According to another embodiment, a pedicle-based distractor assembly includes a pair of headless post assemblies extending from a proximal end to a distal end along a central longitudinal axis. The headless post assembly includes an outer sleeve, an inner sleeve received through the outer sleeve, a screw head clamp at a distal end of the inner sleeve, and drive nut for moving the outer sleeve. When the screw head of a pedicle screw is received in the screw head clamp and the outer sleeve is translated downward, the screw head is clamped by screw head clamp, thereby resulting in a rigid attachment to the pedicle screw.

According to another embodiment, a pedicle-based distractor assembly includes a pair of pre-assembled post assemblies. The pre-assembled post assembly includes an inner post positioned through an outer counter torque sleeve. The inner post threadedly mates to a tulip of a pedicle screw. Once the preassembled post is threaded into place, the post is free to rotate with the tulip. To assist in removal of the post, the outer counter torque sleeve includes a pair of opposed prongs sized and dimensioned to fit in the space between the arms of the tulip. When lowered into position, the prongs of the outer sleeve are receivable into the space between the arms of the tulip and the post is able to rotate independently of the tulip.

According to another embodiment, a pedicle-based distractor and retractor system includes a distraction rack supporting a pair of side arms and a central arm, a connector at the end of each side arm, and a pair of distractor elements engaged with the connectors, each distractor element configured to attach to a pedicle screw to provide pedicle-based distraction, and a medial retraction blade assembly coupled to the central arm. The medial retraction blade assembly includes a medial blade and a medial blade connector. The medial blade connector includes an axial opening, a star grind, and a spring-loaded button. The medial blade includes a shaft receivable in the axial opening of the connector and a star grind corresponding to the star grind of the connector. When locked, the star grinds intermesh and the button engages the shaft of the medial blade.

The pedicle-based distractor and retractor system may include one or more of the following attributes. The shaft may include a tapered distal tip with a circumferential groove, the button defines an opening configured to receive the shaft, and when locked, the button locks into the groove of the shaft. The connector may include a wave spring and a washer positioned between the star grind and the button. The connector may include a gear configured to engage a corresponding worm in a towing assembly. The medial blade may include a slot configured to receive an insert for lengthening and/or widening the medial blade.

According to yet another embodiment, a method of distraction and/or retracting a disc space between first and second vertebrae may include: (a) attaching a first pedicle screw to a pedicle of the first vertebra and a second pedicle screw to a pedicle of a second vertebra; (b) connecting a distraction assembly to the pedicle screws with a pair of distraction elements, such as headless posts, pre-assembled posts, or minimally invasive towers, and distracting the disc space; and (c) optionally retracting soft tissue with a medial retractor blade attached to the distraction assembly.

According to yet another embodiment, a kit may include a distraction assembly with a plurality of modular distraction elements, such as headless posts, pre-assembled posts, or minimally invasive towers, and a medial retraction blade assembly with a medial retraction blade. The kit may include a plurality of pedicle screws or other bone fasteners of varying types and sizes and/or other implants, such as fusion devices. The kit may further include one or more attachment mechanisms, such as table arms, and instruments, such as insertion drivers, for performing the surgery.

BRIEF DESCRIPTION OF THE DRAWINGS

The present embodiments will become more fully understood from the detailed description and the accompanying drawings, wherein:

4

Figure 2:
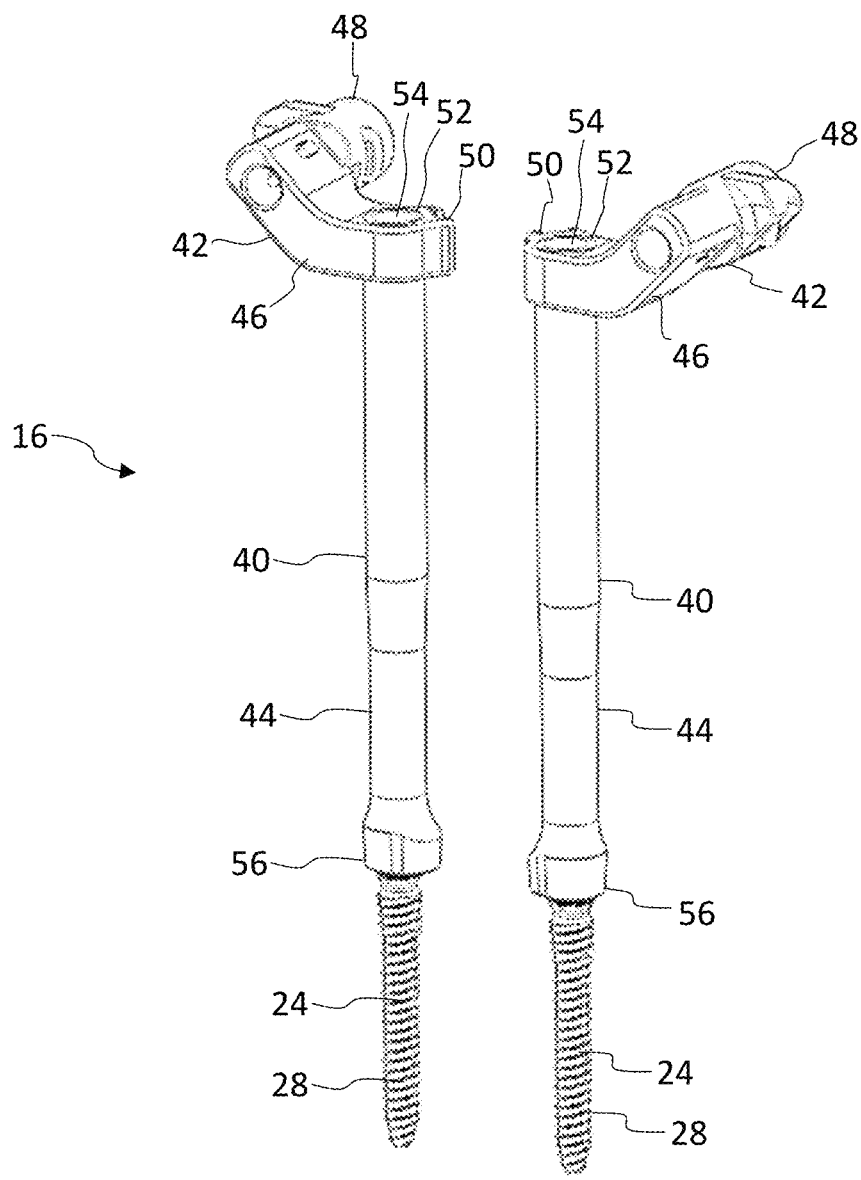
Figure 4A:
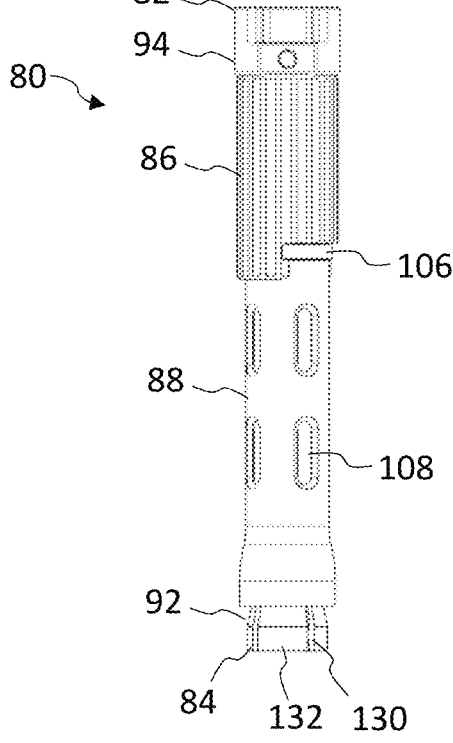
Figure 4B:
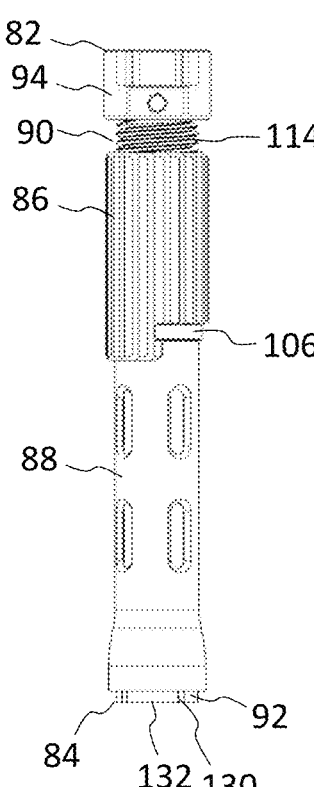
Figures 6A, 6B:
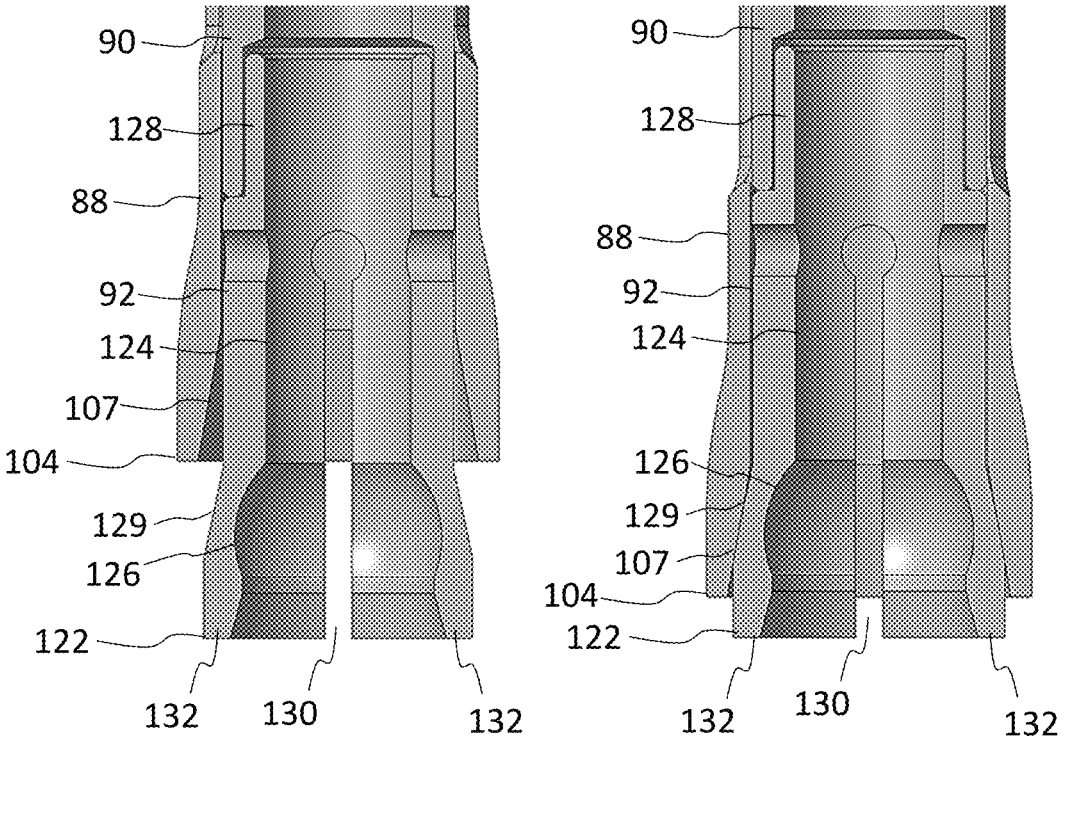
Figures 7A, 7B:
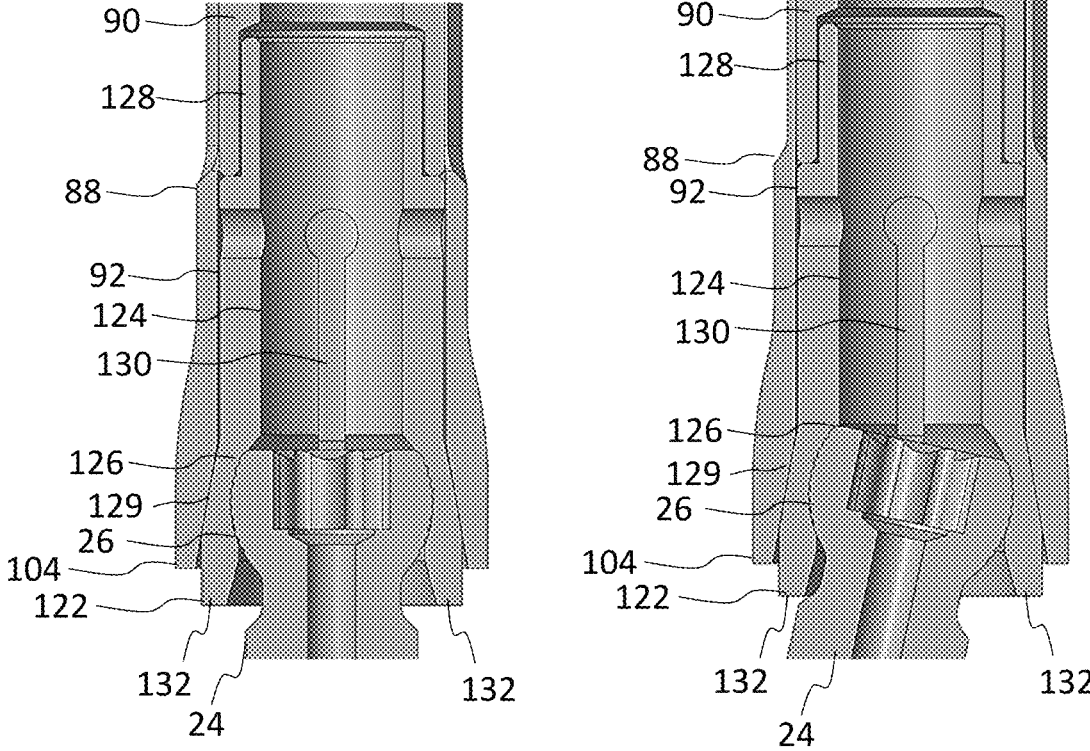
Figure 8A:
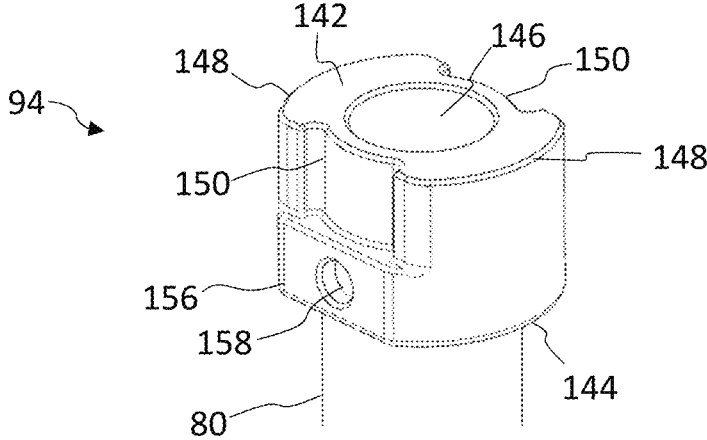
Figure 8B:
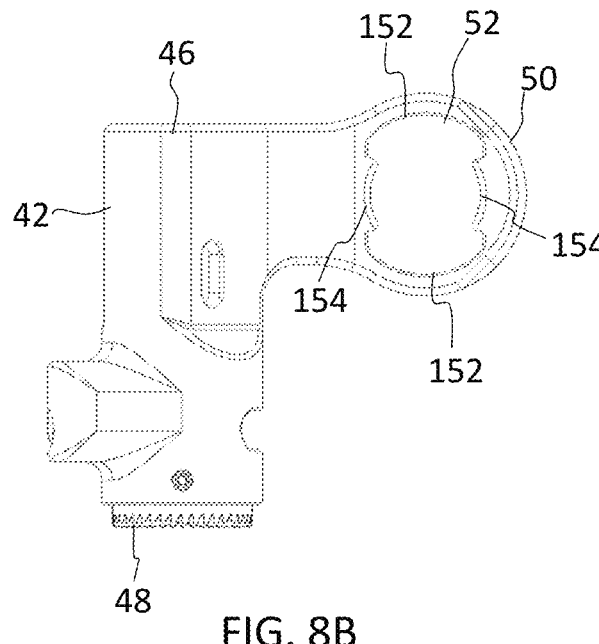
Figure 8C:
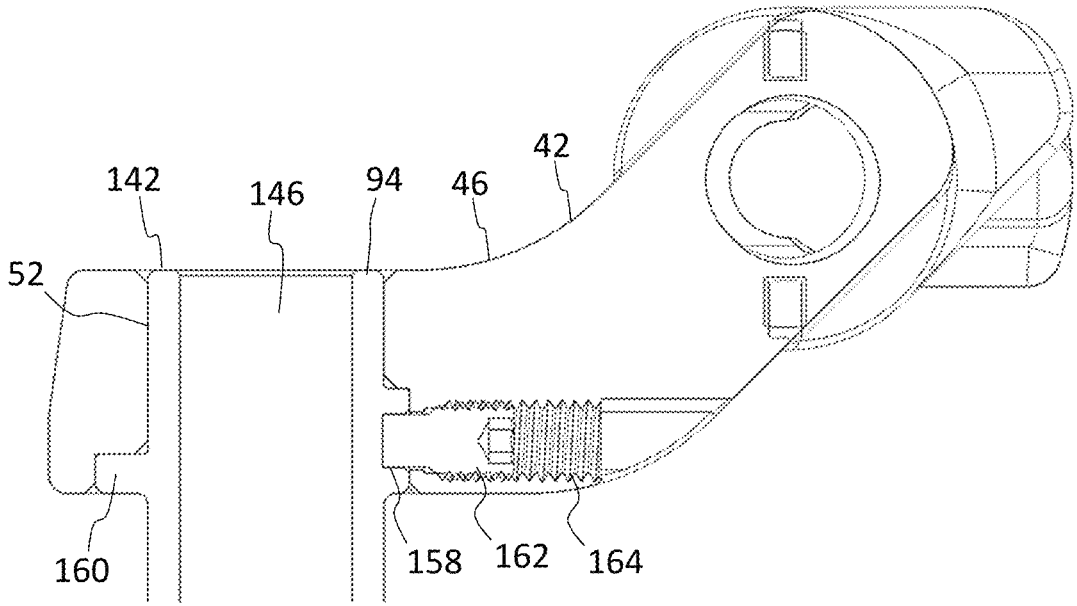
Figure 9:
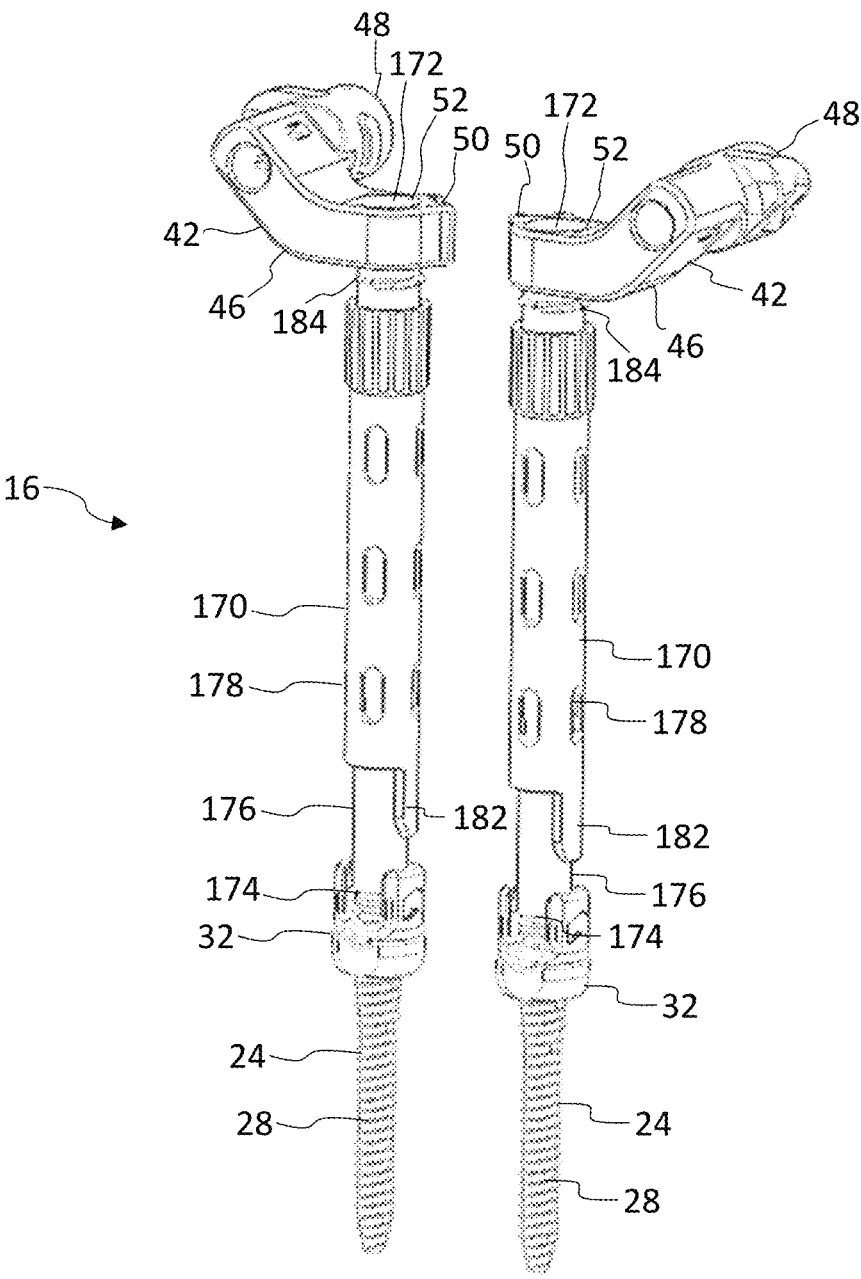
Figure 11:
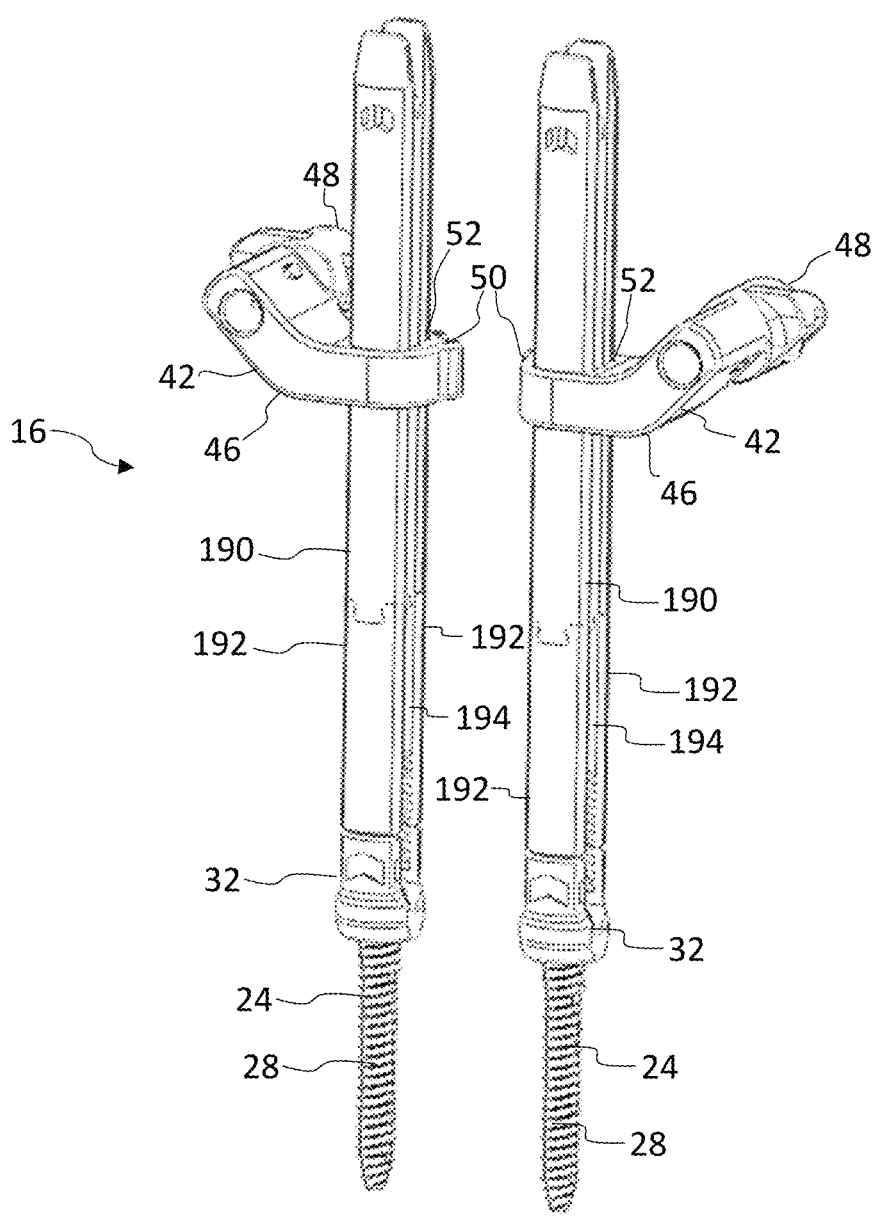
Figure 12A:
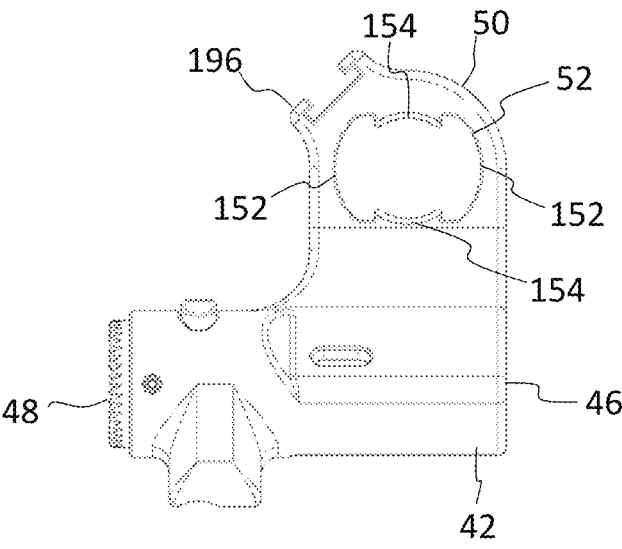
Figure 12B:
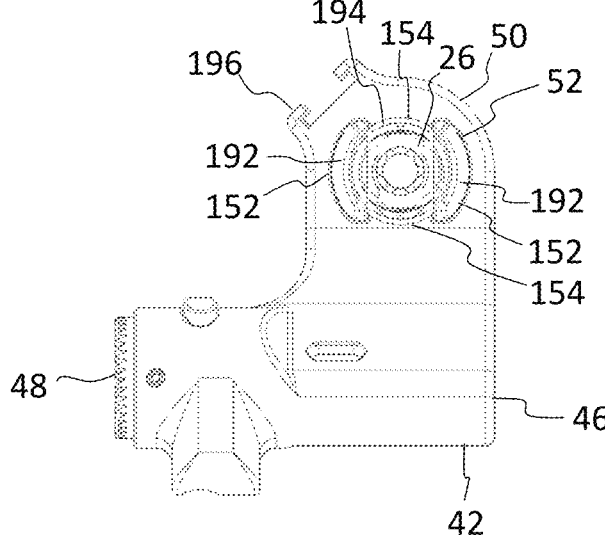
Figure 13:
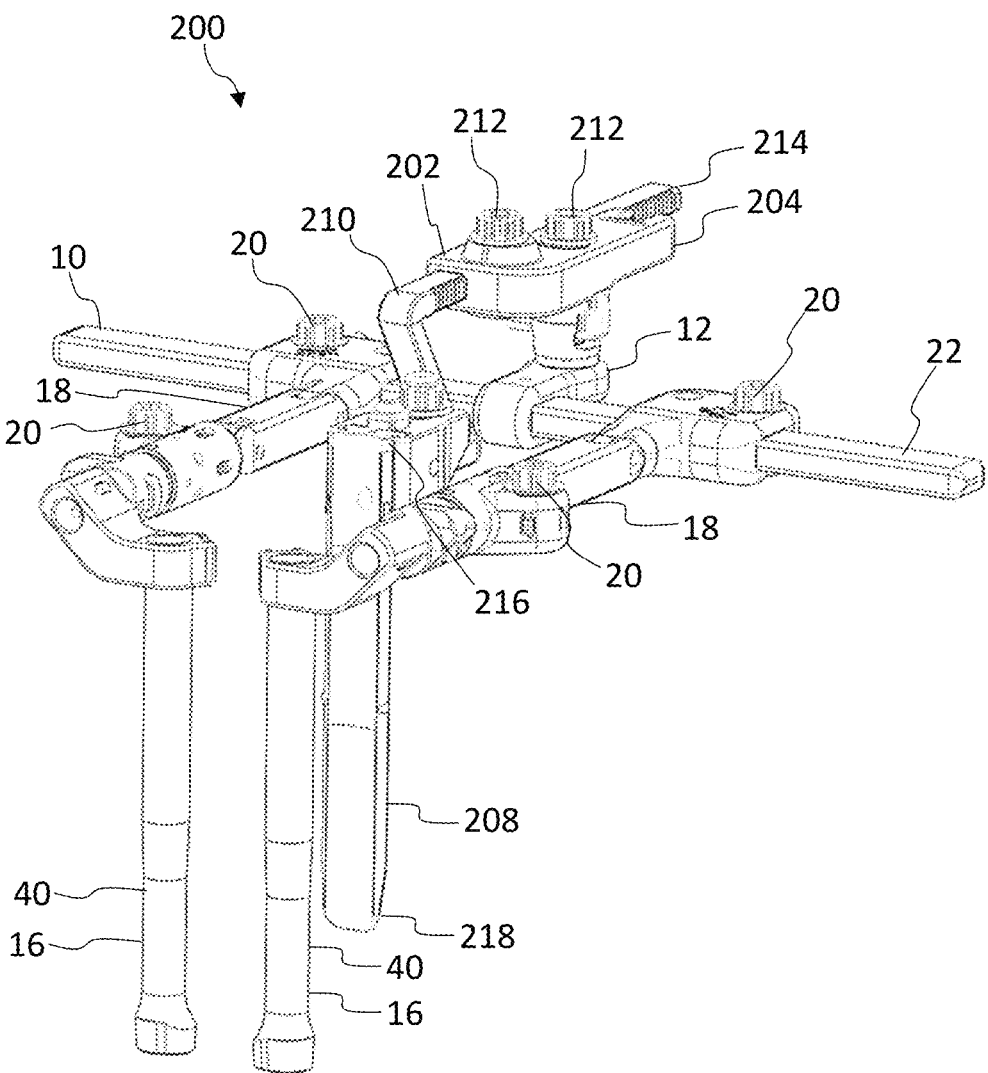
Figure 14:
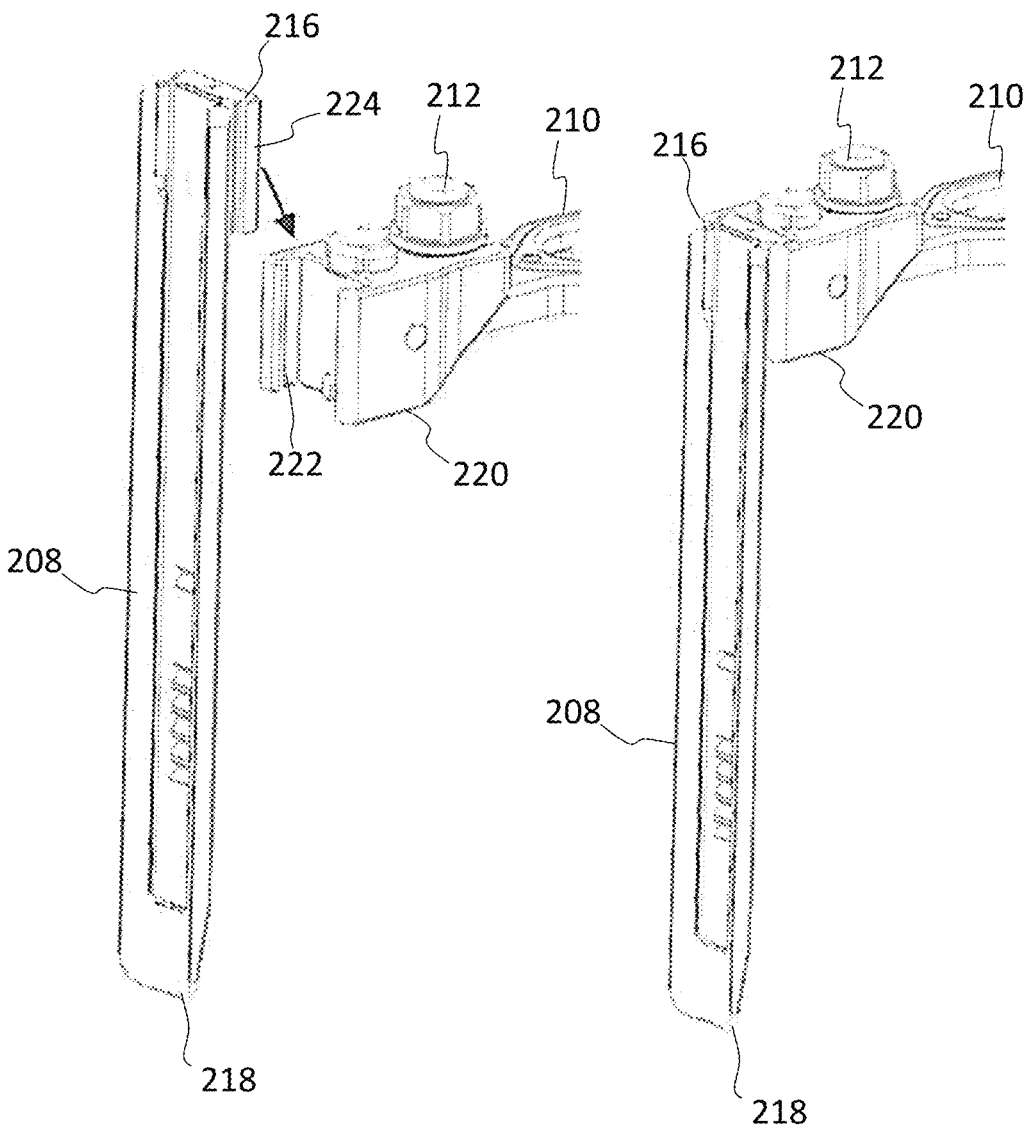
Figure 15:
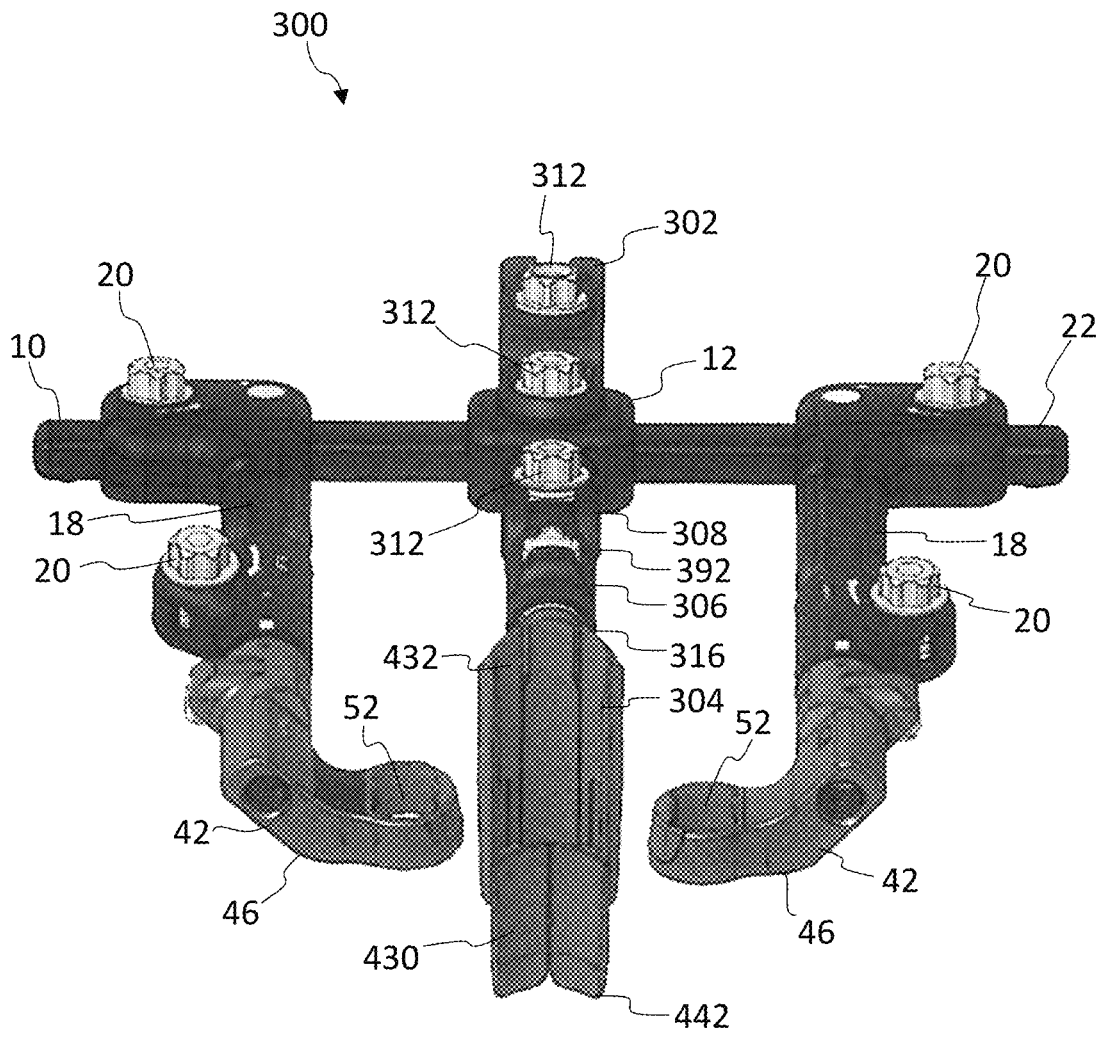
Figure 16A:
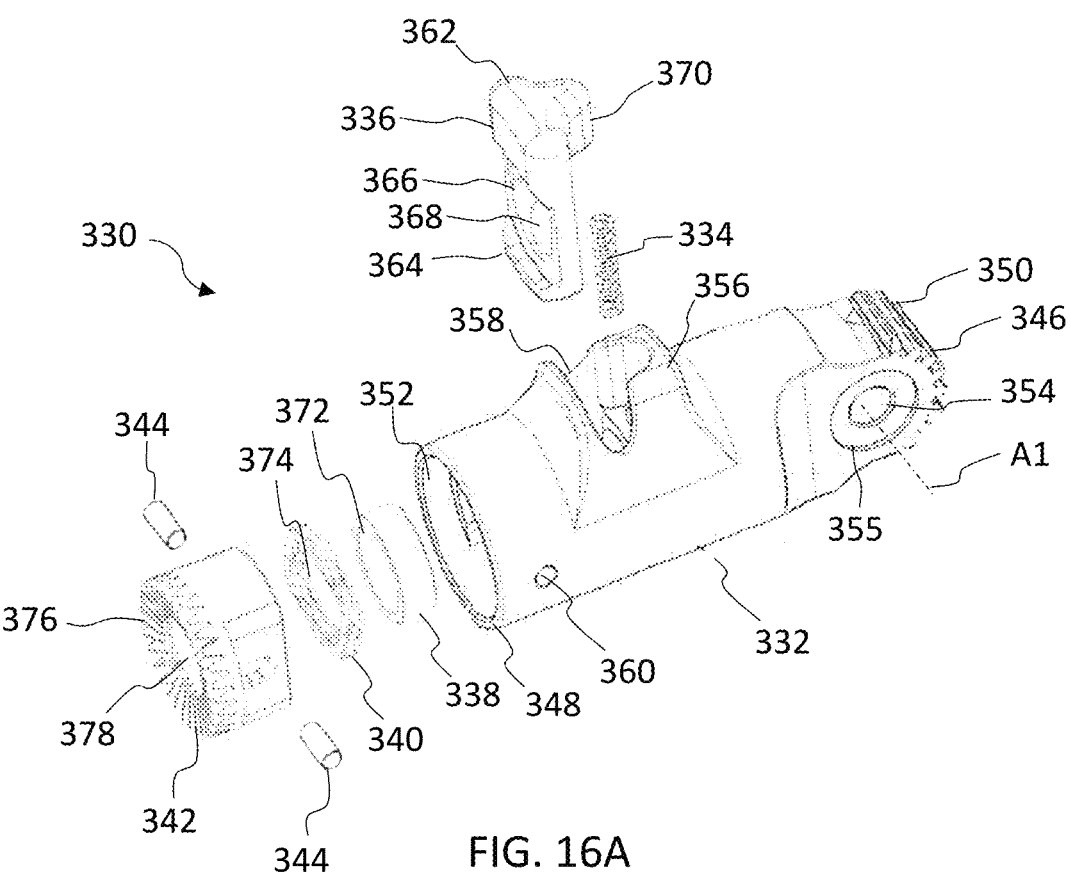
Figure 16B:
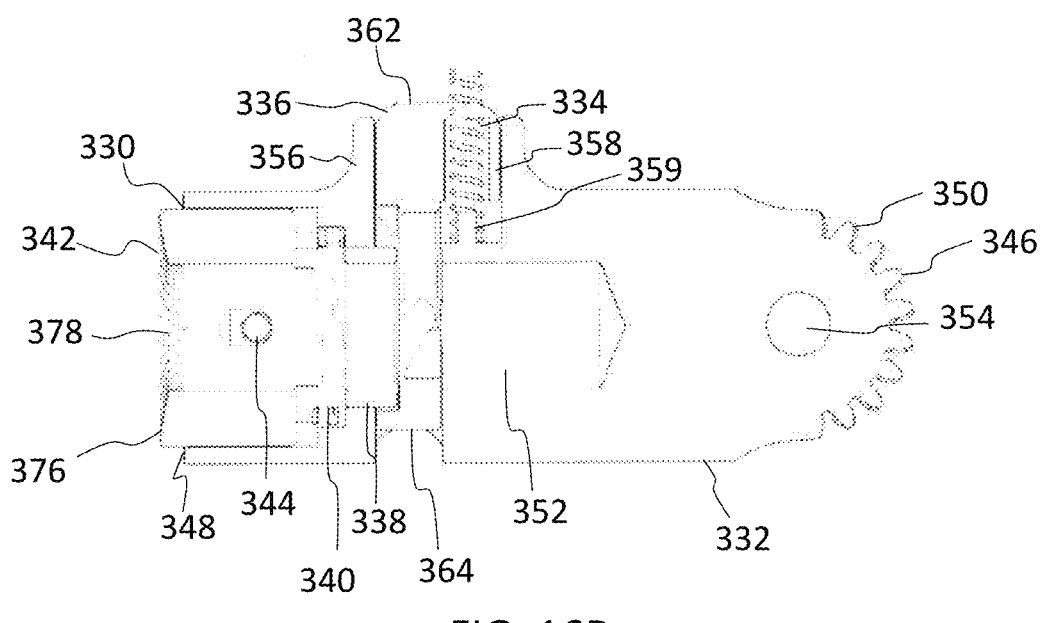
Figure 17:
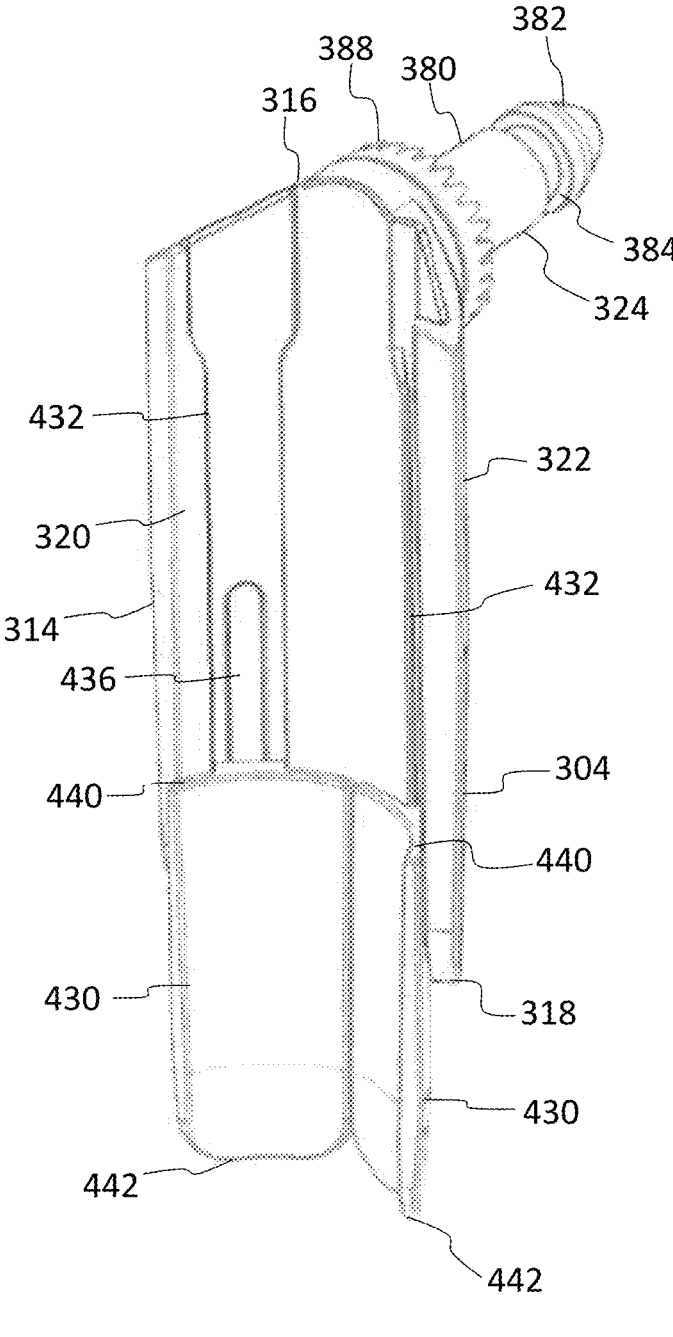
Figure 18A:
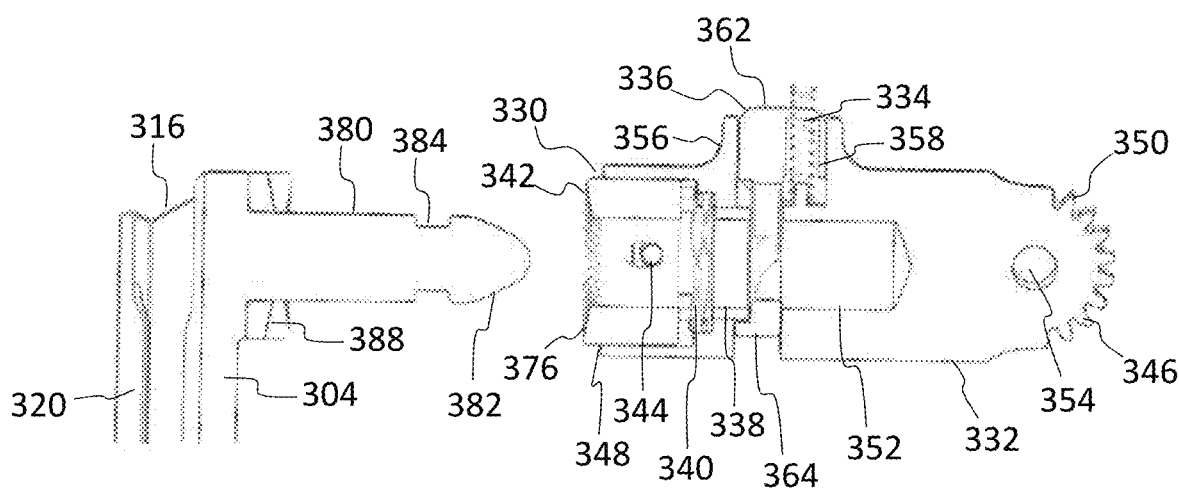
Figure 18B:
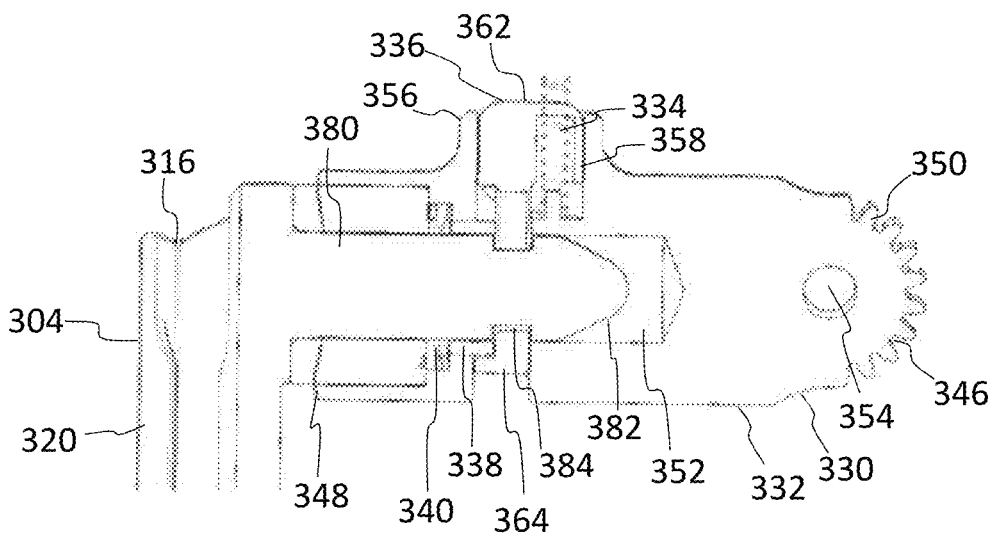
Figure 19A:
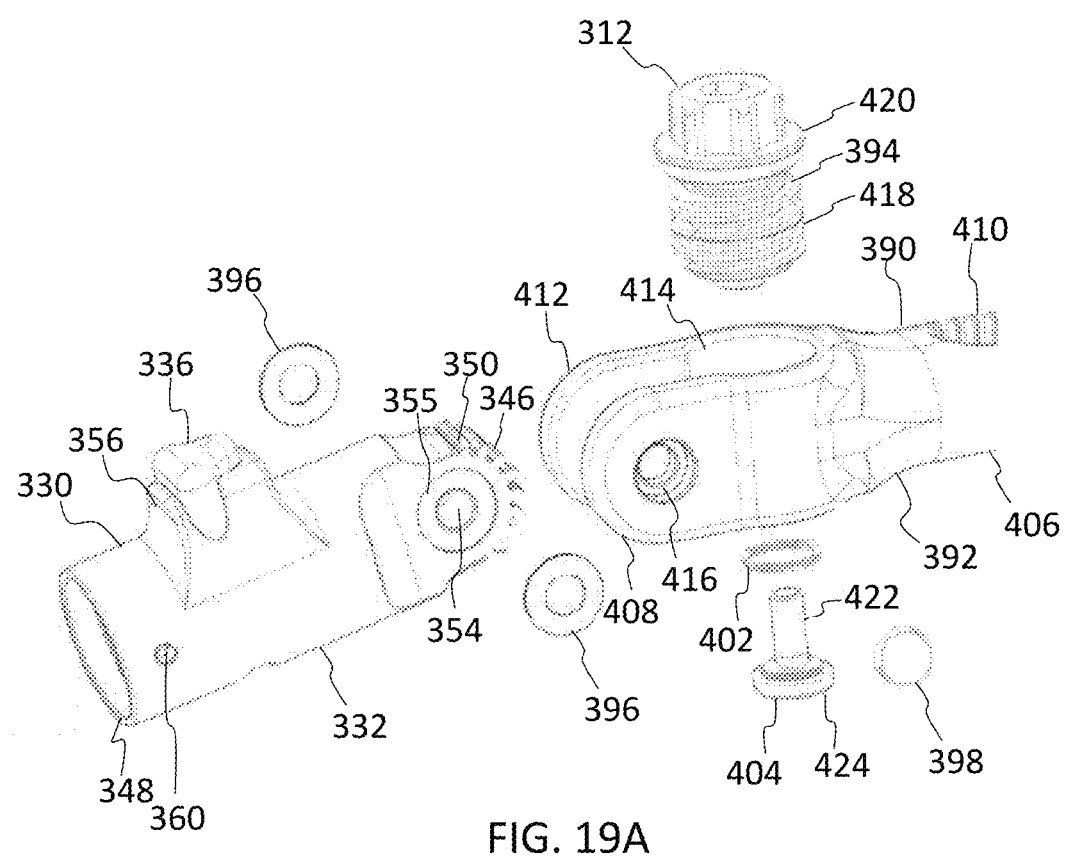
Figure 19B:
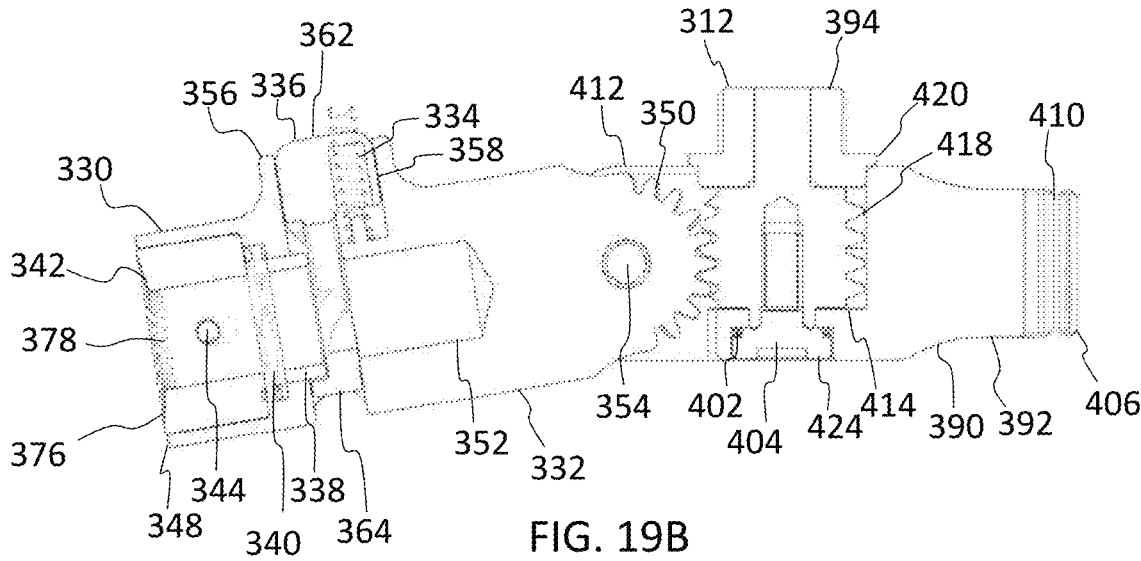
Figures 20A, 20B:
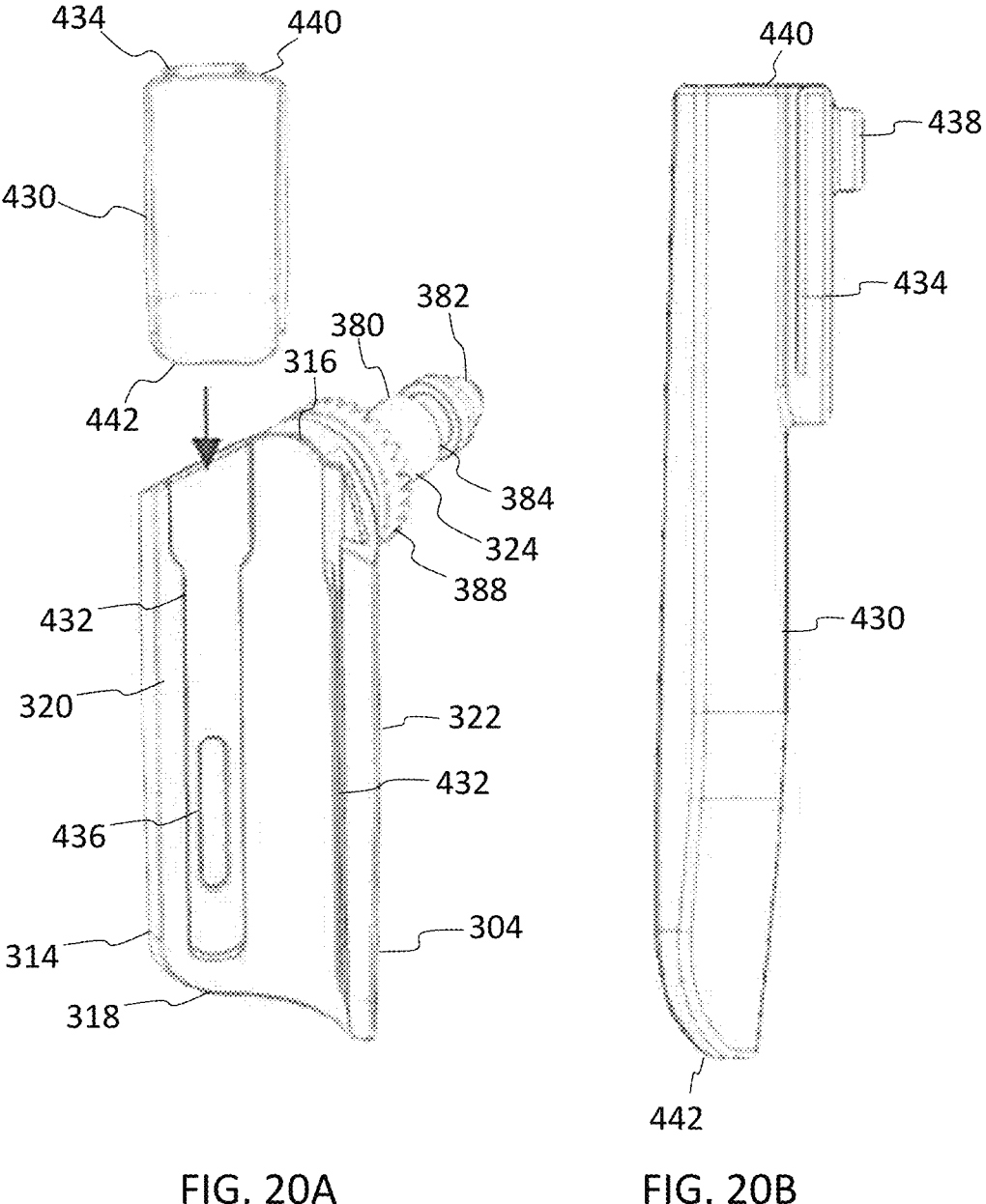

FIG. 1 illustrates a pedicle-based distractor system according to one embodiment;

FIG. 2 shows a pair of headless post distraction elements for use with the distractor system of FIG. 1 according to one embodiment;

FIGS. 3A-3D show cross-sectional and distal views, respectively, of the headless post for capturing the head of a pedicle screw in an open section and a contoured section and a driver instrument engaged with the screw head according to one embodiment;

FIGS. 4A-4B show one embodiment of a headless post distraction assembly in an open position and locked position, respectively;

FIG. 5 shows an exploded view of the headless post distraction assembly according to one embodiment;

FIGS. 6A-6B show the outer sleeve and screw head clamp locking interaction of the headless post distraction assembly in open and locked positions, respectively;

FIGS. 7A-7B show the screw angulation capabilities of the headless post distraction assembly when in the locked position;

FIGS. 8A-8C shows a MIS cap suitable for attaching the proximal end of the distraction post to a MIS sleeve adapter according to one embodiment;

FIG. 9 shows a pair of pre-assembled post distraction elements for use with the distractor system of FIG. 1 according to one embodiment;

FIGS. 10A-10C show perspective and cross-sectional views of the pre-assembled post of FIG. 9 threaded into the tulip of the pedicle screw according to one embodiment;

FIG. 11 shows a pair of MIS sleeve post distraction elements for use with the distractor system of FIG. 1 according to one embodiment;

FIGS. 12A-12B show a MIS sleeve adapter for holding the MIS sleeve post distraction element according to one embodiment;

FIG. 13 illustrates a pedicle-based distractor system with a medial blade retractor system according to one embodiment;

FIGS. 14A-14B show a medial blade with a drop-in connection according to one embodiment;

FIG. 15 illustrates the pedicle-based distractor system with a medial blade retractor system according to another embodiment;

FIGS. 16A-16B show perspective and cross-sectional views, respectively, of a click-in connector for attaching the medial blade according to one embodiment;

FIG. 17 depicts one embodiment of the medial blade assembly;

FIGS. 18A-18B show the connection interaction between the medial blade and the click-in connector according to one embodiment;

FIGS. 19A-19B show perspective and cross-sectional views, respectively, of a towing assembly for adjusting the medial blade according to one embodiment; and FIGS. 20A-20B show examples of translatable blade inserts attachable to the medial blade.

DETAILED DESCRIPTION

Embodiments of the disclosure are generally directed to devices, systems, and methods for distraction and/or retraction using a modular pedicle-based system. Specifically, the modular pedicle-based distractor may include one pair of distraction elements and an optional single blade retractor. The distraction elements may include, for example, headless posts, pre-assembled posts, or MIS sleeves configured to interface with pedicle screws to allow for vertebral distraction. Medial retraction, through the use of a single blade retractor, allows for visualization of the surgical site. The medial retractor blade may be attached to the retractor with a click-in connector and a towing assembly may be used to pivot the blade, thereby retracting soft tissue.

In a spinal fusion procedure, a damaged spinal disc may be removed and replaced with an intervertebral implant (e.g., a cage, spacer, vertebral body replacement, bone graft material, or other prosthetic). The adjacent vertebrae may be stabilized, for example, with a combination of screws and rods. The operation may be performed in an open procedure, semi-open procedure, percutaneous, or in a minimally invasive surgical (MIS) procedure. As part of the procedure, a distractor and/or retractor may be used to establish, enlarge, manipulate, and/or maintain a surgical opening, thereby facilitating the passage of the various implant devices and related tools. In some instances, different distractors/retractors may be used for different surgical approaches (e.g., anterior, posterior, transforaminal, lateral), due to the varying anatomical features unique to each approach. The retractor blades may be used to hold back soft tissue and muscle, and precise angling of the retractor's blades may depend at least in part on various factors, including the particular patient's anatomy and surgeon's preference.

Minimally invasive surgery may be used in attempt to preserve muscular anatomy by only causing disruption where necessary. The benefit of the MIS surgical approach is that it can reduce post-operative pain and recovery time for patients. MIS procedures require smaller incision sizes, resulting in more narrow operating windows when compared to more traditional surgical techniques. An outcome of a narrow operating window is lack of anatomical visualization. It is important to surgeons that anatomical landmarks can be established in order to operate safely and successfully.

The transforaminal lumbar interbody fusion (TLIF) technique is popular in spinal fusion surgery due to the MIS nature of this approach. The procedure consists of targeting the intervertebral space from a trajectory that is 15° to 45 off midline and to then locate the adjacent pedicles as well as the zygapophyseal (facet) joint. Pedicle screws are then inserted and a facetectomy is performed. Facetectomies allow surgeons to gain access to the intervertebral space, but also remove an anatomical landmark. The MIS nature of the TLIF procedure results in the need for consistent and reliable landmarking of anatomical bodies that is continuous throughout the procedure. To ensure the bounds of the operating site are marked, adjacent pedicles can be used as a reference base.

Pedicle distraction is a surgical technique that widens a collapsed disc space. Enlarging the disc space is helpful for completing a thorough discectomy. Discectomies allow for successful placement of an interbody spacer. Since pedicle distraction is based on the pedicle, in addition to its main purpose, it doubles as a landmarking method that pinpoints the surgical safe-zone. With pedicle distraction, there may also be the need for tissue retraction to view the surgical site. Accordingly, devices that can achieve pedicle-based distraction and/or medial retraction may be useful.

Overall, distractor and/or retractor systems disclosed herein may advantageously provide a screw-based distraction and optional medial retraction, resulting in more precise tissue distraction of adjacent bones and retraction of tissue. In particular, a pedicle-based distraction system may include a modular pedicle-based distractor including a pair of distraction elements and an optional single blade retractor.

Once attached to a distractor body, the distraction elements are attached to pedicles to distract the disc space and the medial retractor may retract soft tissue and/or muscle to visualize the surgical site.

As used herein, the terms "proximal" and "distal" are utilized generally with reference to a user (e.g., a surgeon). The distractor may be generally oriented such that the disc space is distracted in the "cephalad" and "caudal" directions. The retractor may be oriented such that the retractor blade is located in a "medial" position. These and other directional terms such as "top" and "bottom" and the like may be used herein for descriptive purposes and do not limit the orientation(s) in which the devices may be used.

The distractor system may include a variety of subcomponents dimensioned to allow for enlargement of a disc space, for example, using a screw-based component to allow for distraction of adjacent bones as well as retraction of soft tissue and/or muscle in order to establish an operative corridor through a patient's skin to a surgical target site. By way of example, the surgical target site may be an intervertebral disc space situated between two adjacent vertebrae. Although particularly suited for use in a transforaminal lumbar interbody fusion (TLIF), it will be readily appreciated by those skilled in the art that the distractor and/or retractor system may be employed in any number of suitable orthopedic approaches and procedures, including but not limited to, anterior, posterior, lateral, anterolateral, or posterolateral approaches to the lumbar spine, cervical spine, or thoracic spine, as well as any non-spine application, such as treatment of bone fractures and the like.

Turning now to the drawing, where like reference numerals refer to like elements, FIG. 1 illustrates a modular distractor system 10 configured for pedicle-based distraction according to one embodiment. The modular nature of the system 10 allow for interchangeability of different types of distraction elements 16: headless posts 40, 80, pre-assembled posts 170, MIS towers 190, etc. Each of the distraction elements 16 interface with their respective pedicle screw type to allow for vertebral distraction. In this embodiment, FIG. 1 illustrates distractor system 10 with headless posts 40, although it will be appreciated that any of the distraction elements 16 described herein may be substituted for posts 40.

The distractor system 10 includes a frame or base 12 supporting a distraction rack 14 that allows for connection to the distraction elements 16. The rack 14 enables cephalad/caudal movement of the distraction elements 16 for vertebral distraction. The rack 14 may be utilized with the distraction elements 16 in one of two main configurations: laying on the patient or connected to a table arm or other supporting structure (not shown). In one embodiment, the base 12 is configured to be attached to a surgical arm, such as a universal arm, which includes enough joints to provide a desired number of degrees of freedom to easily adjust the rack 14 over an incision in a patient. Preferably, the rack 14 is configured to be positioned in a substantially stationary position over the surgical access site.

The distractor elements 16 may be coupled to the distractor rack 14 with one or more moveable arms 18. The arms 18 may provide movement of the distractor elements 16 toward or away from one another. The arms 18 also have the ability to tow the distractor elements 16 clockwise or counterclockwise. The system 10 may include one or more knobs 20 configured to operate each of the elements of the distractor 10. For example, each of the respective knobs 20 may provide for independent movement of each respective distraction element 16 including cephalad/caudal movement, pivoting or towing, or the like as will be recognized by one of ordinary skill in the art.

In one embodiment, the distractor 10 utilizes a rack and pinion system for linear movement. For example, distraction rack 14 linearly translates the side arms 18 and moves distraction elements 16, thereby distracting the bone segments and enlarging the disc space. Examples of rack and pinion system are exemplified in U.S. Pat. Nos. 10,130,348 and 10,285,680, which are incorporated by reference herein in their entireties for all purposes. Although a distraction rack system is exemplified, it is understood that any suitable distractors/retractors known in the art may be used to move the distractor elements 16. Further detail of such devices may be found, for example, in U.S. Pat. Nos. 8,968,363; 8,992,425; 10,278,786; 10,980,528; and 11,109,753, which are incorporated by reference herein in their entireties for all purposes.

Each distraction element 16 is configured to interface with a fastener, such as a pedicle screw 24. The pedicle screw 24 may be inserted into the pedicle of the vertebra, for example, using an MIS or open approach. The fastener or pedicle screw 24 is configured to be removably attached to the distractor element 16. In one embodiment, the pedicle screw 24 may include a head portion 26 (e.g., an enlarged head) at a proximal end configured to engage the distractor element 16 and a shank or bone engagement portion 28 configured to engage bone, for example, having a taper at a distal end. The pedicle screw 24 may have a threaded portion configured to engage the pedicle in a vertebral body. The top of the head 26 defines an instrument recess 30 configured to interface with an instrument, such as a driver 70, to provide torque to the screw 24. The head portion 26 may also be threaded or non-threaded. The pedicle screw 24 may optionally be centrally cannulated along a longitudinal length from the proximal end to the distal end of the screw 24, for example, such that the screw 24 may be guided over a k-wire or the like. The pedicle screw 24 may be configured to provide uni-planar, bi-planar, or poly-axial orientation of the shank 28. In one embodiment, the pedicle screw 24 has a tulip head 32 configured to retain a spinal rod. In this case, the tulip head 32 may permit polyaxial movement relative to the shaft 28. Examples of pedicle screw assemblies are described in U.S. Pat. No. 10,575,877, which is incorporated by reference herein in its entirety for all purposes. It will be appreciated that the fastener 24 may include other fixation members, such as nails, spikes, shims, or the like.

Turning now to FIG. 2, one embodiment of distractor elements 16 for use with the distractor system 10 is shown. In this embodiment, the distractor elements 16 include a pair of headless posts 40. Each headless post 40 includes a connection assembly 42 and a post 44. The connection assembly 42 includes a connector body 46 with a first end 48 configured to interface with the side arm 18 of the distractor 10. For example, the first end 48 of the connector body 46 may include a star grind (e.g., FIG. 16A) or other suitable mechanism for interfacing with the arm 18 or a towing assembly at the end of the arm 18. The connector body 46 may include a spring-loaded button or other suitable mechanism to lock and release the connection assembly 42 to the arm 18. The connector body 46 may be bent or offset to provide for the desired positioning of the distractor posts 44 and the connector body 46 may be configured to provide for towing (e.g., pivoting or rotation) of the distractor posts 44. The connector body 46 includes a second end 50 configured to receive and/or secure the post 44. For example, the second end 50 of the connector body 46 may define a through opening 52 configured to retain the post 44 therein. The post 44 may be secured to the connector body 46 via a set screw 162, press-fit, pin(s), adhesive, or other temporary or permanent attachments. In one embodiment, the connector body 46 acts as a MIS sleeve adapter such that any distractor elements 16 may be connected to the connector body 46.

The post 44 extends from a proximal end 54 to a distal end 56 along a central longitudinal axis. The post 44 may be cannulated with a channel 58 defined through its length. The proximal end 54 of the post 44 is receivable in the opening 52 in the connector body 46. The distal end 56 may define an enlarged screw head receiving portion configured to receive the screw head 26 of the pedicle screw 24.

Turning now to FIGS. 3A-3D, the distal end 56 of the post 44 is shown in more detail. The inner channel 58 is in fluid communication with and terminates at the distal end 56 of post 44 with an enlarged inner pocket or chamber 60. The enlarged inner chamber 60 includes an open bottom for receiving the head 26 of the pedicle screw 24. The chamber 60 includes two screw-retaining sections 62, 64. The primary chamber is an open section 62 that rests on the screw head 26 and allows for free movement and positioning of the post 44. The second chamber is a contoured section 64 that captures the geometry of the screw head 26 when force is applied by the contoured surface 64 in a perpendicular direction to the body of the screw 24. The open section 62 may be generally spherical in shape and may have a volume greater than the volume of the contoured section 64. In particular, the open section 62 may have a depth greater than the depth of the contoured section 64. The contoured section 64 may be spherical in nature with a size and shape generally dimensioned to match the outer geometry of the screw head 26.

FIG. 3A shows the pedicle screw 24 in its open position 62. In the open section 62, the screw 24 is free to translate into the contoured section 64. FIG. 3B shows the screw 24 shifted over to be in contact with the contoured section 64 of the post 44. The arrow between FIGS. 3A and 3B shows the direction that force is applied from the post 44 to the screw head 26 in order for the screw 24 to interface with the post 44. The post 44 may be easily lifted from the screw 24 as long as this force is not applied. In the contoured position 64, if a force perpendicular to the axis of the screw 24 is not applied, the screw 24 will not remain retained by the post 44. The contoured section 64 captures the geometry of the screw head 26 when the force is applied by the contoured surface 64 in a perpendicular direction to the body of the screw 24. The force of this surface against the head 26 of the pedicle screw 24 creates a rigid platform for distraction. If this force is not applied and the screw head 26 is positioned in the pocket 60, the screw 24 will not remain retained by the post 44.

Figure 3C:
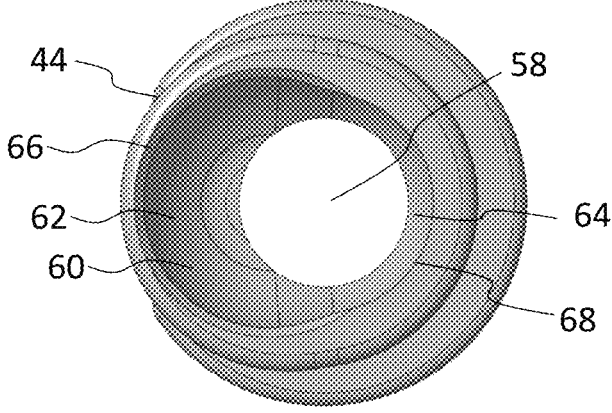

FIG. 3C shows a distal view of the post 44. The contoured section 64 is aligned coaxially with the channel 58 and the open section 62 is offset to the side of the contoured section 64. The edge of the open section 66 may include a beveled edge or chamfer 66, for example, permitting polyaxial movement of the screw 24. The edge of the contoured section 64 may include a slight undercut 68, resulting from a decrease in diameter of the distal opening of the post 44. FIG. 3C shows the diametral reduction that allows for the undercut in the post 44. The undercut 68 of the contour 64 may allow for the screw head 26 to be cupped by the contour 64 in certain configurations.

Figure 3D:
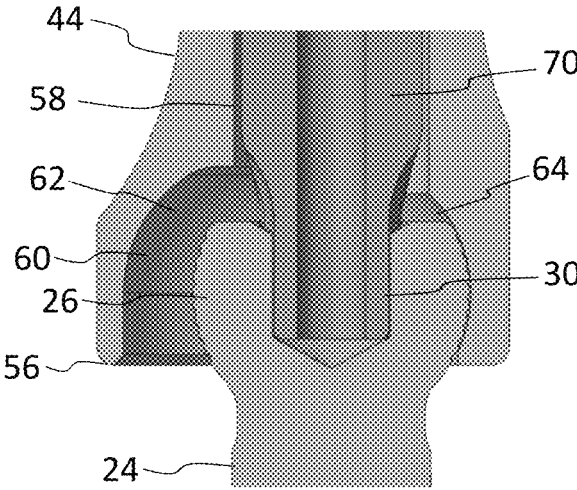

FIG. 3D illustrates driver instrument 70 positioned into recess 30 in the head 26 of the pedicle screw 24 to thereby provide a torque to the screw 24 and/or retain the screw 24 to the post 40. The driver 70 is able to fit through the cannulated portion 58 of the post 44 to reach the screw head 26, which may be useful for screw insertion. In FIG. 3D, the screw 24 is shown in contact with the contoured position 64 of the post 44 with the driver 70 placed through the post 44 and into the screw head 24. With the screw 24, driver 70, and post 44 all aligned axially in conjunction with the contoured section placement of the screw 24, the screw 24 is retained by the post 44 without the addition of a perpendicular distraction force. In one embodiment, the entire construct may be used to implant the pedicle screw 24 in the pedicle of the vertebra.

Turning now to FIGS. 4A-7B, a headless post assembly 80 is shown according to another embodiment. Headless post assembly 80 may connect to connection assembly 42 in a manner similar to headless post 40. This embodiment of the headless post 80 features a more rigid connection, such that the driver 70 does not need to be inserted through the post in order for the screw 24 to be retained. The headless post assembly 80 extends from a proximal end 82 to a distal end 84 along a central longitudinal axis. The headless post assembly 80 includes a drive nut 86, an outer sleeve 88, an inner sleeve 90, a screw head clamp 92, and a MIS cap 94. In this embodiment, the screw head 26 is clamped by the distal end 84 of the post 80 resulting in a rigid screw and post construct.

The outer sleeve 88 extends from a proximal end 102 to a distal end 104 along the central longitudinal axis. The outer sleeve 88 is cannulated through its length and configured to receive the inner sleeve 90. The proximal end 102 of the outer sleeve 88 may include a flange 106 configured to engage the drive nut 86. The distal end 104 of the outer sleeve 88 may be flared or enlarged to receive the screw head clamp 92. An inner surface of the outer sleeve 88 may include one or more angled surfaces 107 configured to interface with outer angled surfaces 129 on the distal end 122 of the screw head clamp 92. The outer sleeve 88 may include one or more windows 108, for example, to allow for sterilization and visualize movement of the inner sleeve 90.

The inner sleeve 90 extends from a proximal end 110 to a distal end 112 along the central longitudinal axis. The inner sleeve 90 may be cannulated through its length to receive an instrument, such as a driver 70. The inner sleeve 90 may include a threaded portion 114 near its proximal end 110. The threaded portion 114 of the inner sleeve 90 is configured to threadedly interface with the drive nut 86. For example, the threaded portion 114 may include one or more external threads configured to mate with corresponding internal threads 138 inside the drive nut 86. The inner sleeve 90 may include a first non-threaded portion 116 between the proximal end 110 and threaded portion 114. The first non-threaded portion 116 may be receivable inside the cap 94. The inner sleeve 90 may include a second non-threaded portion 118 between the threaded portion 114 and the distal end 112 of the inner sleeve 90. The second non-threaded portion 118 may have a diameter greater than the diameter of the first non-threaded portion 116.

The screw head clamp 92 attaches to the distal end 112 of the inner sleeve 90. The screw head clamp 92 extends from a proximal end 120 to a distal end 122 along the central longitudinal axis. The screw head clamp 92 is cannulated and defines a channel 124 therethrough. The channel 124 terminates at chamber 126 configured for retaining the head 26 of the pedicle screw 24. The proximal end 120 includes a collar 128 receivable in an opening in the distal end 112 of the inner sleeve 90. The collar 128 may have a reduced diameter relative to the rest of the screw head clamp 92. The distal end 120 may be flared or enlarged to accommodate the screw head 26. An outer portion of the distal end 120 includes one or more outer angled surfaces 129 configured to interface with corresponding inner angled surfaces 107 inside the outer sleeve 88. The screw head clamp 92 defines one or more slits 130 through the side wall and in fluid communication with the central channel 124 therethrough. The slits 130 may extend from the distal end 122 toward the collar 128 to define one or more spring tabs 132. The slits 130 may be arranged equidistantly around the screw head clamp 92 or at any suitable locations. In one embodiment, the screw head clamp 92 includes four spring tabs 132 oriented about a central axis. When the outer sleeve 88 is translated downward, the screw head clamp 92 compresses around the screw head 26, thereby resulting in a rigid connection.

The drive nut 86 attaches to the proximal end 110 of the inner sleeve 90 and the proximal end 102 of the outer sleeve 88. The drive nut 86 extends from a proximal end 134 to a distal end 136 along the central longitudinal axis. The drive nut 86 is cannulated therethrough and defines an internally threaded portion 138 near the proximal end 134. The internally threaded portion 138 of the drive nut 86 mates with the external threads 114 of the inner sleeve 90. The distal end 136 of the drive nut 86 includes a radial slot 140, such as T slot, cut through the face of the drive nut 86 at its proximal end 136. The radial slot 140 mates with the flange 106 at the proximal end 102 of the outer sleeve 88. An outer surface of the drive nut 86 may have ridges or grooves, for example, configured to be gripped by a user. Rotation of the drive nut 86 translates the inner sleeve 90 through the outer sleeve 88, thereby allowing for clamping of the screw head clamp 92 about the head 26 of the screw 24. The open position is when the drive nut 86 is threaded up and the locked position is when the drive nut 86 is threaded down. The locking mechanism works through the interaction between the outer sleeve 88 and the screw head clamp 92.

The headless post components may be assembled together in this order: drive nut 86, outer sleeve 88, inner sleeve 90, screw head clamp 92, and MIS cap 94. The drive nut 86 may have the radial T-slot 140 cut through one face that captures the upper flange 106 of the outer sleeve 88. The drive nut 86 and outer sleeve 88 are able to rotate independently. Once connected, the assembled drive nut 86 and outer sleeve 88 are threaded onto the inner sleeve 90 such that the distal end 104 of the outer sleeve 88 is above the distal end 112 of the inner sleeve 90. The screw head clamp 92 is then position into the inner sleeve 90 and may be welded in place. The drive nut 86 is then threaded towards the distal end 112 of the inner sleeve 90 such that the proximal end 110 of the inner sleeve 90 can be placed through the MIS cap 94 and may be welded therein. Although welding is exemplified, any suitable attachment may be used. This assembled construct forms the rigid headless post assembly 80 for securing the pedicle screw 24.

As shown in FIGS. 4A and 6A, the post 80 is in its unlocked position. The outer sleeve 88 is raised above the screw head clamp 92. In the open position, the screw head 26 is free to be inserted or removed from the distal chamber 126 inside the screw head clamp 92. In FIGS. 4B and 6B, the post 80 is in its locked position. The outer sleeve 88 is lowered onto the screw head clamp 92. As the outer sleeve 88 is driven down by the drive nut 86, the angled surfaces 107, 129 of the outer sleeve 88 and screw head clamp 92 come into contact. As the outer sleeve 88 is threaded down onto screw head clamp 92, the spring tabs 132 splay inwards resulting in a clamping force on the screw head 26. The inner portion 126 of the screw head clamp 92 may include a spherical contour that matches the head 26 of the screw 24. As best seen in FIGS. 7A-7B, this spherical contour is run out towards the top, allowing for the screw 24 to be positioned at various angles within the construct even when locked. The driver 70 can only be placed through the construct in the axially aligned position. The construct with the driver 70 can be used to implant the screw 24. The off-axis alignment configuration may be useful once the screw 24 has been placed and alternative orientation of the post 80 is desired for distraction purposes.

As best seen in FIG. 8A, the MIS cap 94 is configured to interface with a corresponding opening 52 in the connector body 46, thereby securing the post 80 to the distractor 10. The cap 94 may include a proximal end or upper face 142 and an opposite distal end or lower face 144. The cap 94 may define a central through opening 146 between the upper and lower faces 142, 144 along the central longitudinal axis. The through opening 146 is configured to receive the non-threaded portion 116 of the inner sleeve 90 through the lower face 144 of the cap 94. Although headless post assembly 80 is exemplified, it will be appreciated that the cap 94 may be used with the other distractor elements 16. For example, in the case of headless post 40, the proximal end 54 of the post 44 may be replaced with or positioned in cap 94 as a distraction post connection feature.

The outer profile of the cap 94 is configured to mimic a corresponding opening 52 in the connector body 46. In this manner, the connection assembly 42 may function as an MIS sleeve adapter. Because the MIS profile of the sleeve matches that of the proximal end of the distractor elements 16, the headless posts 40, 80, pre-assembled posts 170, MIS sleeves 190, etc. may all be used with the same connection assembly 42. In particular, the cap profile may mimic an MIS tower 190, which allows all of the various types of distraction elements 16 to be interchangeably used with the same connection assembly 42.

In one embodiment, the cap 94 has a bow-tie like shape that mimics a similar shape of opening 52. In particular, the cap 94 may include a pair of opposed wings 148 defined by opposite recesses 150. The wings 148 may have convex curved side surfaces that fit corresponding concave curves 152 in opening 52. The wings 148 may extend between the upper and lower faces 142, 144 of the cap 94. The opposite recesses 150 may be indented into the body while also providing convex curved side surfaces that fit in corresponding concave curves 154 in opening 52. The opposite curves 154 may be oriented 90° relative to opposite curves 152. The recesses 150 may be provided along an upper portion of the cap 94. A lower portion of the cap 94 aligned with one recess 150 may include a flat face 156 with a bore 158. The opposite side of the cap 94 may include a ledge or shelf 160 receivable in a corresponding notch in the connector body 46. As best seen in FIG. 8C, the cap 94 may be retained in opening 52 through connector body 46 via shelf 160 and/or set screw 162. The set screw 162 is threaded through bore 164 and one end is receivable in bore 158 in cap 94. The placement and location of the post 80 within the sleeve 46 may be controlled by the shelves 160 and flats 156 that are present on both the cap 94 and sleeve 46. The overall construct forms a rigid connection suitable for vertebral distraction when connected to a distraction assembly, such as distractor rack system 10.

Turning now to FIG. 9, another embodiment of distractor elements 16 for use with the distractor system 10 is shown. In this embodiment, the distractor elements 16 include a pair of pre-assembled posts 170. The pre-assembled post assembly 170 may connect to connection assembly 42 in a manner similar to headless posts 40, 80. Each pre-assembled post assembly 170 extends from a proximal end 172 to a distal end 174 along a central longitudinal axis. The pre-assembled post assembly 170 may include an inner sleeve or post 176 positioned through an outer sleeve or counter torque sleeve 178. In this embodiment, the post assembly 170 is attached to the tulip 32 of pedicle screw 24 to allow for vertebral distraction.

Referring now to FIGS. 10A-10C, the preassembled post 176 interacts with the screw 24 through the threads on the tulip 32. As best seen in FIG. 10A, the distal end 174 of the post 176 includes an exterior threaded portion 180 that matches the interior threads of the preassembled tulip 32. Once the preassembled post 176 is threaded into place, the post 176 is free to rotate with the tulip 32. This may be useful for non-parallel distraction of the distractor elements 16. If parallel distraction is desired, an instrument, such as driver 70, may be placed through the cannulation of the post 176. This can also be useful for accessing the recess 30 in the screw head 26 for screw insertion.

To assist in removal of the post 176, the post 176 may be placed through the outer counter torque sleeve 178. As best seen in FIG. 10C, the distal end of the counter torque sleeve 178 includes a pair of opposed prongs 182 sized and dimensioned to fit in the space between the arms of the tulip 32. The outer sleeve 178 is free to rotate and translate along the inner sleeve 176. When lowered into position, the prongs 182 of the outer sleeve 178 are received into the space between the arms of the tulip 32. When the counter torque sleeve 178 is dropped into place and held at the top (to prevent rotation), the post 176 is able to rotate independently of the tulip 32. When not in use, the counter torque sleeve 178 is raised upward. As shown in FIG. 10B, a threaded portion 184 may be provided at the top of the post 176 to interface with a corresponding thread inside the outer sleeve 178, thereby retaining the outer sleeve 178 at the top of the post 176. The threaded interface 184 may be a double-start thread or other suitable mating surfaces to secure the outer sleeve 178 relative to the inner sleeve 176.

Turning now to FIG. 11, another embodiment of distractor elements 16 for use with the distractor system 10 is shown. In this embodiment, the distractor elements 16 include a MIS tower 190. The MIS tower 190 may include a pair of tulip extenders 192 attached to or integrally formed with the arms of the tulip head 32 with a gap therebetween. The MIS extenders 192 may be configured to retract tissue and provide an unobstructed channel 194 for insertion of tools, such as a screw driver or other suitable instrumentation. The extenders 192 are configured to be removable from the tulip 32 such that after use, the extenders 192 may break away and be removed from the tulip 32. Examples of such extenders are described in more detail in U.S. Pat. No. 10,398,454, which is incorporated by reference herein in its entirety for all purposes.

Similar to headless posts 40, 80 and pre-assembly post 170, each MIS tower 190 may connect to the distractor 10 using connection assembly 42. In this embodiment, the connection assembly 42 acts as a MIS sleeve that interacts with the screw 24 through the MIS tower 190. The extenders 192 are receivable through the opening 52 in the connector body 46. The extenders 192 may be moveable through opening 52 such that the connector body 46 is not attached to the proximal end of the MIS tower 190. In other words, the connector body 46 may be located at any suitable location along the length of the MIS tower 190. The sleeve 42 is slid over the tower 190, which enables distraction.

With emphasis on FIGS. 12A-12B, the MIS adapter or sleeve 42 defines an open profile 52 that matches that of the outer profile of tower 190. Similar to the connector opening 52 shown in FIG. 8B, the opening 52 defines wing-like recesses with opposite concave curves 152 configured to receive each of the extenders 192. The opening 52 also defines indentations with opposite curves 154 for maintaining access through the channel 194 between the extenders 192. In this manner, an instrument, such as driver 70, is able to access the top of the screw head 26. The connector 46 may optionally include an attachment area 196, for example, defining a slot for retaining an optional retraction blade. The overall construct forms a moveable connection suitable for vertebral distraction when connected to a distraction assembly, such as distractor rack system 10. The distractor rack system 10 may enable cephalad/caudal movement and/or towing of the towers 190 for vertebral distraction.

Turning now to FIG. 13, a distractor and retractor system 200 is shown according to one embodiment. In this embodiment, the distractor system 10 is combined with a retraction system 202. This provides a compact package of vertebral distraction with medial retraction. The modular nature of the system 200 allow for interchangeability of different types of distraction elements 16: headless posts 40, 80, pre-assembled posts 170, MIS towers 190, etc., in combination with the retraction system 202. In this embodiment, FIG. 13 illustrates distractor and retractor system 200 with headless posts 40 although it will be appreciated that any of the distraction elements 16 described herein may be substituted for posts 40.

The distraction rack 22 may be connected to a retraction base 204. For example, the retraction base 204 may be releasably coupled to the distractor base 12 with attachment shaft 206 projecting upwardly from base 12 (shown in FIG. 1). In this manner, the retraction base 204 may be positioned above the distraction base 12 and distraction rack 22 to support retraction blade 208. Broadly, the retraction base 204 provides a scaffold to hold the various components together and one or more mechanisms for operating the retraction system 202. The capability to fasten the retraction system 202 to the distraction system 10 creates versatility for surgeon preference, providing a multitude of effective applications for the device.

The base 204 provides a mechanism to retract tissue and/or muscle and expand the operative corridor by moving blade 208. In one embodiment, the retraction base 204 may utilize a single blade 208 to retract tissue. The blade 208 may be a medial blade configured to provide visualization of the surgical site. The base 204 may include arm 210 configured to support and move blade 208. The base 204 may include one or more knobs 212, similar to knobs 20, configured to operate each of the elements of the retractor 202. For example, each of the respective knobs 212 may provide for independent movement of the blade 208 including medial/lateral movement, pivoting or towing, or the like.

In one embodiment, medial retraction is achieved through a self-locking rack and pinion system for linear movement. For example, the retractor 202 may utilize a retraction rack 214 to translate arm 210 and move blade 208, thereby retracting tissue. The rack and pinion system may be the same or similar to the one used for the distraction system 10. Although a retraction rack system is exemplified, it is understood that any suitable distractors/retractors may be used to move the retractor blade 208 to its desired position.

When present, the medial retraction blade 208 may allow for visualization of the surgical site. In general, the retractor blade 208 has a first, proximal end portion 216 configured to engage with the arm 210 and a second, distal end portion 218 configured to retract tissue. The blade 208 also includes an inner face, an outer face, and a longitudinal axis running the length of the blade 208 from the proximal end 216 to the opposite distal end 218. Different blade geometries may be used based on the patient anatomy and surgeon preference. The type, size, and shape of the surgical retractor blade 208 may be selected as well as changed or renewed during a surgical procedure.

The overall system 200 includes modular pedicle-based distractor 10 including multiple styles of distraction elements 16 and a single blade retractor 202. The modular system 200 allows for pedicle distraction and/or medial retraction, for example, for TLIF procedures. The unique screw interface geometry of each post 40, 80, 170 and sleeve 46 allows for modularity between the devices. The distraction elements 16 may be fixed position devices, which provide rigidity to the overall distraction assembly 10. The rigidity also provides more tactile feedback with respect to the screws and distraction forces. Pedicle-based distraction, through the use of distraction posts 40, 80, 170 or MIS towers 190, identifies anatomical landmarks while widening the intervertebral disc space. Medial retraction, through the use of the single retractor blade 208, allows for visualization of the surgical site. The resultant configuration of the system 200 is based on surgeon preference, and it will be appreciated that the pedicle-based distraction system 10 and medial retraction system 202 may be used separately, individually, or together in combination.

Turning now to FIGS. 14A-14B, a drop-in style connection of a static medial blade 208 is shown according to one embodiment. For example, the end of arm 210 may include an attachment member 220 configured to retain the blade 208. The attachment member 220 may include one or more tracks 222 for retaining corresponding rails 224 on the proximal end 216 of the blade 208. For example, the attachment member 220 may include a pair of opposite female tracks 222 for receiving corresponding male rails 224 on the edge of the blade 208. In this manner, the rails 224 slide into the tracks 222 in the attachment member 220, thereby securing the static blade 208 to the end of arm 210. It will be appreciated that the track and rail system may be reversed on the components or otherwise configured to secure the blade 208 to the attachment member 220.

Turning now to FIG. 15, a distractor and retractor system 300 is shown according to another embodiment. In this embodiment, the distractor system 10 is combined with a retraction system 302. Retraction system 302 is similar to retraction system 202 except the base 12 of the distractor 10 forms part of the retraction system 302, thereby streamlining and simplifying the overall footprint of the device. Similar to system 200, the modular nature of system 300 allows for interchangeability of different types of distraction elements 16 combined with the retraction system 302. In this embodiment, FIG. 15 illustrates distractor and retractor system 300 with the distraction elements 16 omitted for clarity although it will be appreciated that any of the distraction elements 16 may be positioned in openings 52 for pedicle-based distraction in the manner described herein.

The medial retraction system 302 includes a medial blade 304 and a medial blade connector 306. The connector 306 provides an intuitive way of connecting the medial blade 304 to the retractor in a manner that will prevent retracted tissue from escaping from underneath the blade 304. The retraction system 302 may be coupled to the distraction base 12. A central arm 308 may couple base 12 to connector 306. The retraction system 302 may include one or more knobs 312, similar to knobs 20, 212, configured to operate each of the elements of the retractor 302. For example, each of the respective knobs 312 may provide for independent movement of the blade 304 including medial/lateral movement, pivoting or towing, or the like.

When present, the medial retraction blade 304 may allow for visualization of the surgical site. In general, the retractor blade 304 has a first, proximal end portion 316 configured to engage with the connector 306 and a second, distal end portion 318 configured to retract tissue. The blade member 304 also includes an inner face 320, an outer face 322, and a longitudinal axis running the length of the blade 304 from the proximal end 316 to the opposite distal end 318. Different blade geometries may be used based on the patient anatomy and surgeon preference. The type, size, and shape of the surgical retractor blade 308 may be selected as well as changed or renewed during a surgical procedure.

Turning now to FIGS. 16A-16B, a click-in connector 330 is shown according to one embodiment. In this embodiment, the medial blade assembly 304 is attached to the arm 308 of the retractor system 302 using click-in connector 330 replacing the drop-in track and rail system shown in FIGS. 14A-14B. The click-in connector 330 includes a connection body 332, spring 334, button 336, retaining washer 338, wave spring 340, star grind 342, and pins 344.

The connector body 332 extends from a first end 346 configured to engage with a portion of the retractor system 302 (e.g., towing assembly 390) to a second end 348 configured to engage with medial blade 304 along a longitudinal axis. The connector body 332 includes a gear 350 at the first end 346 and an axial opening 352 at the second end 348. The gear 350 includes a plurality of gear teeth provided about a gear segment at the first end 346 from an upper surface to a lower surface of the connector body 332. The gear 350 is configured to engage a corresponding worm gear 394 on the towing assembly 390. The gear 350 is able to pivot about an axis of revolution A1 defined by opening 354. The axis of revolution A1 may be generally perpendicular to the longitudinal axis of the connector body 332. Both sides of the opening 354 are surrounded by recesses 355 configured to receive respective bellville washers 396 (see FIG. 19A), which along with screw 398, pivotally secure the connector body 332 to the towing assembly 390.

The axial opening 352 at the opposite end 348 of the connector body 332 is sized and configured to house the inner components 338, 340, 342 and receive at least a portion of the shaft 380 of the blade 304 (e.g., the portion of the shaft 380 projecting into the second end 348 of the connector body 332). The connector body 332 includes an upper bump out 356 for retaining the button assembly 336. The upper bump out 356 may enlarge the height and width of the connector 332. The upper bump out 356 defines a cavity 358 configured to receive button 336 and spring 334. The cavity 358 may be aligned generally perpendicular to the longitudinal axis of the connector 332. The connector body 332 also defines one or more pin bores 360 configured to receive pins 344 which secure the star grind 342 to the distal end 348 of the connector body 332.

The button 336 includes an upper surface 362 configured to be depressed by a user and a lower surface 364 receivable in the cavity 358 in the connector 332. One face of the button 336 may define a notched area 366 configured to receive a portion of the washer 338. The notched area 366 defines a through opening 368 configured to receive the shaft 380 of the blade 304. The lower surface 364 may include an overhang, pointing toward the star grind 342, configured to hook under the washer 338. The opposite face of the button 336 may define an upper projection 370 with a pocket for receiving one end of the spring 334. The other end of spring 334 may be secured in the cavity 358, for example, with a dowel 359 or other suitable mechanism.

The star grind 342, wave spring 340, and washer 338 fit into the opening 352 in connector 332. The washer 338 includes a ring with a through-opening 372 for receiving shaft 380 of the blade 304. The wave spring 344 includes a coiled wave spring, such as a single turn or multi-turn wave spring, with a through-opening 374 for receiving shaft 380 of the blade assembly 304. The star grind 342 includes a distal face 376 with a plurality of protrusions (e.g., bumps, peaks, teeth, and/or ridges) and/or receptacles (e.g., valleys, channels, depressions, and/or grooves), for example, in a star grind pattern, extending radially around through-opening 378. The star grind face 376 may be configured to intermesh and/or interdigitate with the corresponding star grind surface 388 on the blade 304. The star grind interface 376, 388 allows for the blade 304 to be locked rotationally with the connection assembly 306.

The click-in connector assembly 330 may be assembled as follows. The spring 334 is placed on the dowel 359 of connection body 332. Button 336 is then placed into cavity 358 of connection body 332 such that spring 334 sits in the pocket 370 of button 336. While pushing downward on button 336, retaining washer 338 is pressed into the connection body 332 in order to retain button 336. Wave spring 340 is then placed into connection body 332 followed by star grind 342. Pins 344 are then pressed into connection body 332 in order to retain the star grind 342. A cross-section of the assembled connector 330 is shown in FIG. 16B.

With further emphasis on FIG. 17, the blade member 304 includes a blade portion 314 and a connection portion 324 configured to interface with the click-in connector 330. The connection portion 324 may include a shaft 380 projecting outwardly from the outer face 322 of the blade portion 314 near the proximal end 316 of the blade 304. The shaft 380 may be aligned generally transverse (e.g., perpendicular) to the longitudinal axis of the blade portion 314. The shaft 380 may be generally elongate and/or at least partially cylindrical and is receivable in the axial opening 352 in the click-in connector 332. The free end of the shaft 380 may include a tapered distal tip 382 with a circumferential channel or groove 384 on an exterior surface thereof. The groove 384 may extend partially or entirely around the circumference of the shaft 380 and is configured interface with the opening 368 in button 336. The blade 304 includes a star grind 388 sized and dimensioned to correspond and interface with the star grind 376 on the connector 330. The star grind 388 may be formed by a plurality of protrusions (e.g., bumps, peaks, teeth, and/or ridges) and/or receptacles (e.g., valleys, channels, depressions, and/or grooves) interspersed therebetween, which correspond to the opposite star grind 342. The star grind 380 may extend radially outward from the shaft 380. In addition to the automatic spring-loaded button mechanism 336, the blade member 304 is held in place by interference between the star grind 388 on the blade member 304 with corresponding star grind 342 on the connector 330.

FIGS. 18A-18B show the connection interaction between the medial blade 304 and the click-in connector 330. As best seen in FIG. 18A, the shaft 380 is aligned with the axial opening 352 in the connector 332. The tip 382 of the shaft 380 is inserted through opening 378 in the star grind 342, through opening 374 in the wave spring 340, through opening 372 in the washer 338, through opening 368 in the button 336, and into axial opening 352 through the connector body 332. As shown in FIG. 18B, the shaft 380 is receivable through the connector body 332 and is free to rotate about the axis of the shaft 380. When locked, the star grinds 376, 388 intermesh and the button 336 locks into groove 384, thereby securing the shaft 380 to the connector body 332.

Turning now to FIGS. 19A-19B, the connector 330 is coupled to towing assembly 390 to provide towing capabilities to blade 304. This is accomplished by the gear teeth 350 that are cut into the back of connector body 332, which interact with the worm-gear style towing assembly 390. The towing assembly 390 includes medial rack or towing body 392, worm 394, bellville washers 396, screw 398, wave spring 402, and set screw 404.

The medial rack or towing body 392 includes a proximal end 406 and a distal end 408 with a longitudinal axis therebetween. The proximal end 406 includes a threaded portion 410 for securing the towing body 392 to the medial arm 308. Alternatively, the towing body 392 may be integrally formed with the medial arm 308 or otherwise configured to couple to the retraction system 302 (e.g., base 12). The distal end 408 includes a pair of arms 412 with a gap therebetween configured to receive the proximal end 346 of the connector body 332. The arms 412 may be vertically oriented such that the gap extends from the distal end 408 and between the upper and lower surfaces of the body 392. The gap terminates as a through cavity 414 configured to receive worm gear 394. The cavity 414 may be generally cylindrical in shape to mimic the outer shape of the worm 394. The arm 412 defines one or more threaded openings 416 for retaining screw 398 to pivotally secure the connector body 332 to the towing assembly 390.

The worm 394 is receivable in cavity 414 in the towing body 392. The worm 394 may include a lower worm gear 418 configured to interface with the gear 350 of the connecting body 332. The worm gear 418 may have a generally cylindrical body with one or more exterior threads. The gears 350, 418 have non-parallel, non-intersecting bodies oriented 90° to each other. The worm 394 acts as the driving component such that threads of the worm gear 418 advance the teeth of the gear 350, thereby pivoting connector body 332 about the axis of revolution A1. The upper portion of the worm 394 includes an instrument engaging surface, such as knob 312. Knob 312 may be hex, round, square, or otherwise configured to be rotated by an instrument. A flange 420 may separate the upper knob 312 from the lower worm gear 418. The flange 420 may rest in the top of the towing body 392, thereby concealing the internal components. The worm 394 is attached to the towing body 392 with wave spring 402 and set screw 404. Set screw 404 may have a shaft 422 with an enlarged head 424. The shaft 422 is receivable in an opening through the bottom of the worm gear 418. The wave spring 402 rests against the enlarged head 424, which seats into a recess in the towing body 392, thereby securing the worm 394 to the towing body 392 while still allowing rotation movement.

To assemble the connector body 332 to the towing assembly 390, place the bellville washers 396 into the respective recesses 355 around opening 354 of connector body 332. The bellville washer 396 or conical spring washers may have a frusto-conical shape. Then, place the connector body 332 into the slot between the arms 412 of towing body 392. Fasten the connector body 332 by placing screw 398 through both the towing body 392 and the connector body 332 and thread into the towing body 392. To assemble the worm gear 394 to the towing body 392, place worm 394 into the towing body 392 by threading to the gear portion 350 of connector body 332. Place wave spring 402 onto set screw 404 and thread set screw 404 into worm 394 until set screw 404 is flush with towing body 392. A cross-section of the assembled state is shown in FIG. 19B. In this manner, rotation of the worm 394 (e.g., via knob 312) causes pivotal movement of connecting body 332 and attached blade 304, thereby providing towing of medial blade 304.

Turning now to FIGS. 20A-20B, the blade 304 may be enhanced with one or more blade inserts 430 configured to increase the length and/or width of the blade 304. The blade insert 430 connects into blade portion 314 and may function as a translating component, for example, at the distal end 318 of the blade 304. Depending upon preference, the blade 304 may retain a singular translating insert 430, two translating inserts 430, or more than two translating inserts 430. Any embodiment that contains two or more translating inserts 430 maintains independent translation amongst the components. In FIG. 17, two independently translating inserts 430 are attached at the distal end 318 of the blade 304. FIG. 20A depicts a single insert 430 being inserted into the blade portion 314 and FIG. 20B depicts an alternate style of blade insert 430.

The inner face 320 of the blade portion 314 defines one or more slots 432 that extend longitudinally down the length of the blade 314. As shown in FIG. 20A, the inner face 320 may define a pair of slots 432, for example, positioned near the lateral sides of the blade 314. The slots 432 may be generally parallel with one another. Each slot 432 may be open at the proximal end 316 of the blade 314 and extend a length toward the opposite end 318 but stopping short of distal end 318. The slot 432 may be a T-slot with a wider neck near the proximal end 316 of the blade 314. The T-slot 432 is configured to receive a linear bar 434 on the back of the insert 430. Each T-slot 432 may define a translation aperture 436 along its longitudinal length. These translating inserts 430 translate within T-slots 432 and may also have a pin 438 on the back that fits within the translation aperture 436 of the medial blade 304.

Each blade insert 430 includes a proximal end 440 and a distal end 442. The blade insert 430 may be curved or contoured about its longitudinal axis. The blade insert 430 may have any suitable width and length to modify the blade portion 314. In one embodiment shown in FIG. 20A, the blade insert 430 may have a width less than the width of the blade portion 314 and a length shorter than the length of the blade portion 314. In this manner, a pair of blade inserts 430 may be retained side by side, as shown in FIG. 17, to extend the overall length of the blade 304. In the embodiment shown in FIG. 20B, the blade insert 430 may have a width less than the width of the blade portion 314 and a length longer than the length of the blade portion 314. It will be appreciated that any suitable blade insert 430 may be used for the desired surgical outcome.

When the insert 430 is assembled to the blade portion 314, the distal end 442 of the insert 430 aligns with the proximal end 316 of the blade portion 314. As best seen in FIG. 17, once the bar 434 is aligned with slot 432 and the insert 430 slides downward, the distal tip 442 of the insert 430, depending on its length, may protrude downward past the distal end 318 of the blade portion 314. FIG. 20A shows how the translating inserts 430 of the medial blade 304 are positioned in the blade 314 through the T-slot 432. Once the insert 430 is placed far enough into the blade 314, the pin 438 of the insert 430 engages with the aperture 436 of the blade 304. This interaction locks the insert 430 into the blade 314 within its range of motion. The range of motion is dependent on the length of the aperture 436, thereby providing for linear translation of the insert(s) 430.

Components of all of the devices disclosed herein may be made of any suitable materials including metals (e.g., titanium), metal alloys (e.g., stainless steel, cobalt-chromium, and titanium alloys), ceramics, polymers (e.g., polyether ether ketone (PEEK), polyphenylene sulfone (PPSU), polysulfone (PSU), polycarbonate (PC), polyetherimide (PEI), polypropylene (PP), polyacetals, or mixtures or co-polymers thereof), and/or combinations thereof. In some embodiments, the devices may include radiolucent and/or radiopaque materials. The components can also be machined and/or manufactured using any suitable techniques.

Advantageously, the distractor and/or retractor systems and associated devices described herein can be used with a number of different implants and devices. For example, the distractor/retractor systems can be used to provide access to a surgical site such that a fusion device, such as a cage or spacer, or standalone device, can be provided. In addition, the distractor/retractor systems can be used to provide access to various other devices, including but not limited to rods, screws (e.g., pedicle screws, cortical screws, etc.), plates and various other implants that are used in spine surgery or other orthopedic applications.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is intended that the components of the various devices disclosed above may be combined or modified in any suitable configuration.

What is claimed is:

1. A pedicle-based distractor and retractor system comprising:
   a distraction base configured to be attached to a surgical arm, the distraction base supporting a distraction rack;
   the distraction rack supporting a medial arm and pair of side arms, each side arm comprising a distal end comprising a connector, and a proximal end independently adjustable along the distraction rack;
   a pair of distractor elements each adapted to attach at a proximal end thereof to one of the connectors and at a distal end thereof to a pedicle screw to provide pedicle-based distraction, wherein each distractor element includes a headless post, a pre-assembled post, or a minimally invasive tower, and wherein the distractor elements are modular such that different types of distractor elements are interchangeable with the connectors; and
   a retraction blade assembly adapted to adjustably couple to the medial arm and including:
   an elongate retraction blade having an adjustable length and/or width;
   a locking shaft extending laterally from the retraction blade;
   a click-in connector adapted to attach to the distraction base and having a spring loaded axial opening for receiving and locking the locking shaft of the retraction blade, the retraction blade configured to freely rotate about the axial opening until the locking shaft is locked to the spring loaded axial opening,
   wherein: the click-in connector includes a star grind; the retraction blade includes a star grind corresponding to the star grind of the click-in connector such that when the retraction blade is locked to the click-in connector, the star grinds intermesh with each other to rotationally lock the retraction blade to the click-in connector.

2. The distractor and retractor system of claim 1, wherein the click-in connector includes a spring loaded button that defines the axial opening, the axial opening of the button configured to receive and lock the locking shaft.

3. The distractor and retractor system of claim 2, wherein the locking shaft includes a tapered distal tip with a circumferential groove, and the axial opening of the button locks into the circumferential groove of the locking shaft.

4. The distractor and retractor system of claim 2, wherein the click-in connector includes: a wave spring and a washer positioned between the star grind and the button.

5. The distractor and retractor system of claim 1, wherein the click-in connector includes a wave spring and a washer positioned coaxially in the axial opening.

6. The distractor and retractor system of claim 1, wherein the click-in connector includes a circumferential gear configured to engage a corresponding worm in a towing assembly attached to the distraction base.

7. The distractor and retractor system of claim 6, wherein the circumferential gear is configured to allow rotation of the click-in connector relative to the distraction base.

8. The distractor and retractor system of claim 1, wherein the retraction blade includes a slot configured to receive an insert for lengthening and/or widening the retraction blade.

9. The distractor and retractor system of claim 8, wherein the retraction blade includes a translating aperture to allow the insert to translate.

10. A pedicle-based distractor and retractor system comprising:
   a distraction base configured to be attached to a surgical arm, the distraction base supporting a distraction rack;
   the distraction rack supporting a pair of side arms and a central arm, the side arms each comprising a distal end comprising a connector, and a proximal end configured to independently slide along the distraction rack;
   a pair of distractor elements each adapted to attach at a proximal end thereof to one of the connectors and at a distal end thereof to a pedicle screw to provide pedicle-based distraction, wherein each distractor element includes a headless post, a pre-assembled post, or a minimally invasive tower, and wherein the distractor elements are modular such that different types of distractor elements are interchangeable with the connectors;
   a medial retraction blade assembly adapted to attach to the central arm and including:
   an elongate medial blade including a slot configured to receive an insert for lengthening and/or widening the medial blade;
   a locking shaft extending laterally from the medial blade;
   a click-in connector adapted to attach to the distraction base and having a spring loaded axial opening for receiving and locking the locking shaft of the medial blade, the medial blade configured to freely rotate about the axial opening until the locking shaft is locked to the spring loaded axial opening,
   wherein: the click-in connector includes a star grind; the medial blade includes a star grind corresponding to the star grind of the click-in connector such that when the medial blade is locked to the click-in connector, the star grinds intermesh with each other to rotationally lock the medial blade to the click-in connector.

11. The distractor and retractor system of claim 10, wherein the click-in connector includes a spring loaded button that defines the axial opening, the axial opening of the button configured to receive and lock the locking shaft.

12. The distractor and retractor system of claim 11, wherein the locking shaft includes a tapered distal tip with a circumferential groove, and the axial opening of the button locks into the circumferential groove of the locking shaft.

13. The distractor and retractor system of claim 11, wherein the click-in connector includes: a wave spring and a washer positioned between the star grind and the button.

14. The distractor and retractor system of claim 10, wherein the click-in connector includes a wave spring and a washer positioned coaxially in the axial opening.

15. The distractor and retractor system of claim 10, wherein the click-in connector includes a circumferential gear configured to engage a corresponding worm in a towing assembly attached to the distraction base.

16. The distractor and retractor system of claim 15, wherein the circumferential gear is configured to allow rotation of the click-in connector relative to the distraction base.

17. The distractor and retractor system of claim 10, wherein the medial blade includes a translating aperture to allow the insert to translate.

* * * * *